(12) United States Patent
Tong et al.

(10) Patent No.: US 11,435,333 B2
(45) Date of Patent: Sep. 6, 2022

(54) PH-SENSITIVE NANOPARTICLES FOR DETECTING AND PREVENTING FOOD SPOILAGE

(71) Applicant: University of Florida Research Foundation, Inc., Gainesville, FL (US)

(72) Inventors: Zhaohui Tong, Newberry, FL (US); Suguna Jairam, Gainesville, FL (US)

(73) Assignee: University of Florida Research Foundation, Inc., Gainesville, FL (US)

(*) Notice: Subject to any disclaimer, the term of this patent is extended or adjusted under 35 U.S.C. 154(b) by 1282 days.

(21) Appl. No.: 15/863,463

(22) Filed: Jan. 5, 2018

(65) Prior Publication Data

US 2018/0284092 A1   Oct. 4, 2018

Related U.S. Application Data

(63) Continuation-in-part of application No. PCT/US2016/035706, filed on Jun. 3, 2016.
(Continued)

(51) Int. Cl.
   *G01N 33/02* (2006.01)
   *G01N 21/78* (2006.01)
   (Continued)

(52) U.S. Cl.
   CPC ............ *G01N 33/02* (2013.01); *B01J 13/185* (2013.01); *B65D 77/24* (2013.01); *B65D 81/34* (2013.01);
   (Continued)

(58) Field of Classification Search
   None
   See application file for complete search history.

(56) References Cited

U.S. PATENT DOCUMENTS

| 4,180,632 | A  |   | 12/1979 | Ilenda |
| 6,312,679 | B1 | * | 11/2001 | Tomalia ............... C07C 211/29 523/105 |

(Continued)

FOREIGN PATENT DOCUMENTS

| CN | 103113603 A | 5/2013 |
| CN | 103399012 B | 12/2015 |

(Continued)

OTHER PUBLICATIONS

Active chitosane/PVA film with anthocyanines by Pereira et al, Food Hydrocolloids, 43, 2015, 180-188.*
(Continued)

*Primary Examiner* — Tae H Yoon
(74) *Attorney, Agent, or Firm* — Thomas | Horstemeyer, LLP

(57) ABSTRACT

Nanoparticles and compositions thereof are provided for detecting and/or preventing food spoilage. Methods of making the nanoparticles and compositions, and methods of using the nanoparticles and compositions, e.g. in food packaging, are also provided. The nanoparticles can have a hydrophobic core containing a hydrophobic active agent, e.g. a hydrophobic dye and/or an antimicrobial agent, for detecting and/or preventing food spoilage. The nanoparticles can also have a copolymer of a hydrophobic polymer repeat unit, e.g. styrene or lactic acid, and a pH responsive dendrimer repeat unit. The pH responsive dendrimer repeat unit can have a pH responsive amine core having a plurality of branched acrylate arms extending therefrom. The nanoparticles can be chemically stable at neutral pH, and then release the hydrophobic active agent at a pH range indicative of food spoilage. By releasing the hydrophobic dye and/or antimicrobial agent, the nanoparticles can detect and/or inhibit food spoilage.

11 Claims, 7 Drawing Sheets

Related U.S. Application Data

(60) Provisional application No. 62/188,952, filed on Jul. 6, 2015.

(51) Int. Cl.

| | | |
|---|---|---|
| *C08G 83/00* | (2006.01) | |
| *B82Y 30/00* | (2011.01) | |
| *B82Y 40/00* | (2011.01) | |
| *B65D 77/24* | (2006.01) | |
| *B65D 81/34* | (2006.01) | |
| *C09B 67/02* | (2006.01) | |
| *B01J 13/18* | (2006.01) | |
| *C09B 67/46* | (2006.01) | |
| *C09B 67/08* | (2006.01) | |
| *G01N 33/12* | (2006.01) | |

(52) U.S. Cl.
CPC ............... *B82Y 30/00* (2013.01); *B82Y 40/00* (2013.01); *C08G 83/003* (2013.01); *C09B 67/009* (2013.01); *C09B 67/0013* (2013.01); *C09B 67/0097* (2013.01); *G01N 21/78* (2013.01); *G01N 33/12* (2013.01)

(56) References Cited

U.S. PATENT DOCUMENTS

| | | | |
|---|---|---|---|
| 6,593,142 | B2 | 7/2003 | Kelly et al. |
| 8,790,930 | B2 | 7/2014 | Mills et al. |
| 2010/0086482 | A1* | 4/2010 | Tomalia ............... C08G 83/003 424/9.1 |
| 2011/0009641 | A1 | 1/2011 | Anderson et al. |
| 2011/0189291 | A1 | 8/2011 | Yang et al. |
| 2011/0274593 | A1 | 11/2011 | Gorski et al. |
| 2012/0076994 | A1 | 3/2012 | Herlihy et al. |
| 2012/0183452 | A1 | 7/2012 | Schalkhammer |
| 2014/0256545 | A1 | 9/2014 | Velev et al. |
| 2014/0341967 | A1* | 11/2014 | Cooper ............... A61K 9/0019 424/641 |

FOREIGN PATENT DOCUMENTS

| | | |
|---|---|---|
| WO | 2012152531 A1 | 11/2012 |
| WO | 2017007552 A1 | 1/2017 |

OTHER PUBLICATIONS

Kuswandi, "Smart packaging: sensors for monitoring of food quality and safety" published Nov. 30, 2011, Springer Science+Business Media, LLC 2011.
Bamban Kuswandi, et al., "Smart packaging: sensors for monitoring of food quality and safety", Sensing and Instrumentation for Food Quality and Safety (2011), 5:137-146.
International Search Report and Written Opinion for PCT/US16/35706 dated Sep. 1, 2016.
Arvanitoyannis, I., Biliaderis, C.G., Ogawa, H., Kawasaki, N. 1998. Biodegradable films made from low-density polyethylene (LDPE), rice starch and potato starch for food packaging applications: Part 1. Carbohydrate Polymers, 36 (2), 89-104.
Barnes, E.M., Impey, C. 1968. Psychrophilic spoilage bacteria of poultry Journal of Applied Bacteriology, 31(1), 97-107.
Borch, E., Kant-Muermans, M.-L., Blixt, Y. 1996a. Bacterial spoilage of meat and cured meat products. International journal of food microbiology, 33(1), 103-120.
Chen, X., & Gu, Z. (2013). Absorption-type optical pH sensitive film based on immobilized purple cabbage pigment. Sensors and Actuators B: Chemical, 178, 207-211.
Choi, I., Lee, J. Y., Lacroix, M., & Han, J. (2017). Intelligent pH indicator film composed of agar/potato starch and anthocyanin extracts from purple sweet potato. Food chemistry, 218, 122-128.

Weber, C.J. 2000. Biobased packaging materials for the food industry: Status and perspectives, a European concerted action.
Dalgaard, P. 1995. Qualitative and quantitative characterization of spoilage bacteria from packed fish. International Journal of Food Microbiology, 26(3), 319-333.
Dainty, R. 1996. Chemical/biochemical detection of spoilage. International journal of food microbiology, 33(1), 19-33.
Ellis, D.I., Goodacre, R. 2001. Rapid and quantitative detection of the microbial spoilage of muscle foods: current status and future trends. Trends in Food Science & Technology, 12(11), 414-424.
Gram, L., Dalgaard, P. 2002. Fish spoilage bacteria-problems and solutions. Current opinion in biotechnology, 13(3), 262-266.
Gram, L., Huss, H.H. 1996. Microbiological spoilage of fish and fish products. International journal of food microbiology, 33(1), 121-137.
Korkeala, H., Alanko, T., Makela, P., Lindroth, S. 1990. Lactic acid and pH as indicators of spoilage for vacuum-packed cooked ring sausages. International journal of food microbiology, 10(3), 245-253.
Lee, J.-W., Son, S.-M., Hong, S.-I. 2008. Characterization of protein-coated polypropylene films as a novel composite structure for active food packaging application. Journal of Food Engineering, 86(4), 484-493.
Pacquit, A., Frisby, J., Diamond, D., Lau, K.T., Farrell, A., Quilty, B., Diamond, D. 2007. Development of a smart packaging for the monitoring of fish spoilage. Food Chemistry, 102(2), 466-470.
Pacquit, A., Lau, K.T., McLaughlin, H., Frisby, J., Quilty, B., Diamond, D. 2006. Development of a volatile amine sensoi for the monitoring of fish spoilage. Talanta, 69(2), 515-520.
Park, H.J., Chinnan, M.S. 1995. Gas and water vapor barrier properties of edible films from protein and cellulosic materials. Journal of Food Engineering, 25(4), 497-507.
Pereira, V. A., de Arruda, I. N. Q., & Stefani, R. (2015). Active chitosan/PVA films with anthocyanins from *Brassica oleraceae* (Red Cabbage) as time-temperature indicators for application in intelligent food packaging. Food Hydrocolloids, 43, 180-188.
Pexara, E.S., Metaxopoulos, J., Drosinos, E.H. 2002. Evaluation of shelf life of cured, cooked, sliced turkey fillets and cooked pork sausages—'piroski'—stored under vacuum and modified atmospheres at+ 4 and+ 10° C. Meat science, 62(1), 33-43.
Samelis, J., Kakouri, A., Georgiadou, K., Metaxopoulos, J. 1998. Evaluation of the extent and type of bacterial contamination at different stages of processing of cooked ham. Journal of applied microbiology, 84(4), 649-660.
Samelis, J., Kakouri, A., Rementzis, J. 2000. The spoilage microflora of cured, cooked turkey breasts prepared commercially with or without smoking. International journal of food microbiology, 56(2), 133-143.
Schirmer, B., Heir, E., Langsrud, S. 2009. Characterization of the bacterial spoilage flora in marinated pork products. Journal of applied microbiology, 106(6), 2106-2116.
Scheu, P.M., Berghof, K., Stahl, U. 1998. Detection of pathogenic and spoilage micro-organisms in food with the polymerase chain reaction. Food microbiology, 15(1), 13-31.
Smolander, M., Ahvenainen, R. 2003. The use of freshness indicators in packaging. Novel food packaging techniques, 127-143.
Vihavainen, E.J., Björkroth, K.J. 2007. Spoilage of value-added, high-oxygen modified-atmosphere packaged raw beef steaks by Leuconostoc gasicomitatum and Leuconostoc gelidum. International journal of food microbiology, 119(3), 340-345.
Veiga-Santos, P., Ditchfield, C., Tadini, C. 2011. Development and evaluation of a novel pH indicator biodegradable film based on cassava starch. Journal of Applied Polymer Science, 120(2), 1069-1079.
Weber, C., Haugaard, V., Festersen, R., Bertelsen, G. 2002. Production and applications of biobased packaging materials for the food industry. Food Additives & Contaminants, 19(S1), 172-177.

* cited by examiner

PH-SENSITIVE NANOPARTICLES FOR DETECTING AND PREVENTING FOOD SPOILAGE

CROSS-REFERENCE TO RELATED APPLICATIONS

This application is a continuation-in-part of pending Patent Cooperation Treaty (PCT) Application entitled "PH-SENSITIVE NANOPARTICLES FOR DETECTING AND PREVENTING FOOD SPOILAGE" having international application number PCT/US2016/035706 and having an international filing date of Jun. 3, 2016, and claims priority to, and the benefit of, U.S. provisional application entitled "PH-SENSITIVE NANOPARTICLES FOR DETECTING AND PREVENTING FOOD SPOILAGE" having Ser. No. 62/188,952 filed Jul. 6, 2015, the contents of which are incorporated by reference in their entirety.

STATEMENT REGARDING FEDERALLY SPONSORED RESEARCH OR DEVELOPMENT

This invention was made with government support under grant DE-PI0000031 awarded by The United Stated Department of Energy. The government has certain rights in the invention.

BACKGROUND

Food safety is an important issue and a high priority globally placing human and animal health and care under the spotlight. It has been observed that the spoilage of food occurs in stages one indicator of which is a variation in pH as the food material undergoes changes in palatability. The deterioration of food material can therefore be indicated through the various stages of its shelf life when packaged with suitable pH-sensitive smart materials. Stimulus-responsive polymers are high performance polymeric structures that have specific responses to variations in their physical and/or chemical environment. Current research is moving in the direction of nano-scale biomaterials for reliable and cost-effective detection of diseases, pathogens, chemicals, and contaminants of food and other consumables.

It is therefore an object of this disclosure to provide improved materials, compositions, and methods for detecting, inhibiting, and/or preventing food spoilage.

It is a further object of this disclosure to provide methods of making the materials and compositions for detecting, inhibiting, and/or preventing food spoilage.

It is an additional object of this disclosure to provide improved packaged food products containing the materials and compositions for increasing the life of the food product.

SUMMARY

In various aspects nanoparticles and films and compositions thereof are provided for detecting and/or preventing food spoilage. Methods of making the nanoparticles and compositions thereof are also provided, as well as methods of use for detecting and/or preventing food spoilage, e.g. for detecting the presence of one or more food spoilage microorganisms or inhibiting the outgrowth of one or more food spoilage microorganisms.

In one or more exemplary embodiments, nanoparticles for the detection and/or prevention of food spoilage are provided containing a hydrophobic core to encapsulate an hydrophobic active agent, and a copolymer of a hydrophobic polymer repeat unit and a pH responsive dendrimer repeat unit. The hydrophobic active agent can be, for example, a hydrophobic dye, a hydrophobic antimicrobial agent, or a combination thereof. The hydrophobic polymer repeat unit can be a styrene, a methacrylate such as methyl methacrylate, a lactic acid, or a derivative thereof. The pH responsive dendrimer repeat unit can have a structure according to the following formula or a derivative thereof

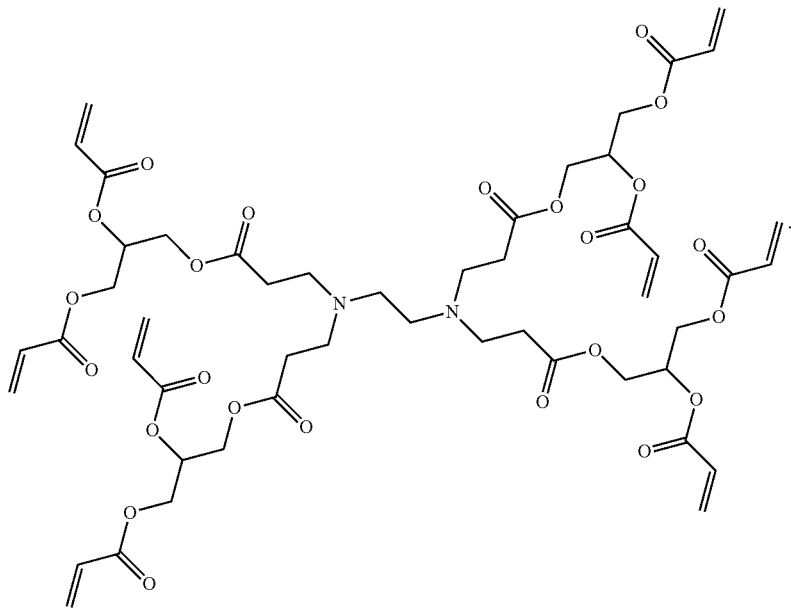

The pH responsive dendrimer repeat unit can have a structure according to the following formula or a derivative thereof

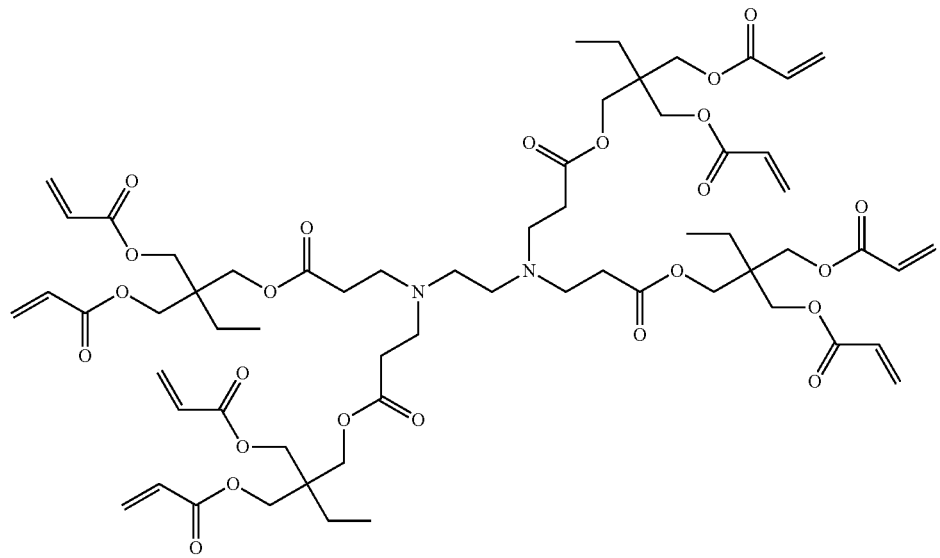

The pH responsive dendrimer repeat unit can be present at an amount from about 5 wt % to 20 wt % based upon the weight of the copolymer. The nanoparticle can be chemically stable and have a diameter of about 50 nm to 200 nm at neutral pH. However, the nanoparticle can release the hydrophobic active agent at a pH range of about 4.5 to 6.7 to indicate or prevent the food spoilage.

In various aspects, nanoparticles are provided having a hydrophobic core containing a hydrophobic active agent; and a copolymer of a hydrophobic polymer repeat unit and a pH responsive dendrimer repeat unit. The pH responsive dendrimer repeat unit can contain a pH responsive amine core having a plurality of branched acrylate arms extending therefrom. Although nanoparticles having a variety of sizes can be prepared, in various aspects the nanoparticles have a diameter of about 50 nm to 250 nm.

A variety of hydrophobic active agents can be in the nanoparticle. In some aspects, the hydrophobic active agent is a hydrophobic therapeutic agent, a hydrophobic prophylactic agent, or a hydrophobic diagnostic agent. The hydrophobic active agent can be a dye, an antimicrobial agent, or a combination thereof.

In various aspects, the hydrophobic polymer repeat unit is selected from the group consisting of a fluorocarbon, a tetrafluoroethylene, a vinylfluoride, a siloxane, a dimethylsiloxane, butadiene, a methacrylate such as methyl methacrylate, ethylene, an olefin, styrene, propylene, and an oligomer thereof.

The pH responsive dendrimer repeat unit can have a pH responsive amine core having a plurality of branched acrylate arms extending therefrom. In some aspects, the pH responsive amine core is selected from the group consisting of ethylene diamine, propane-1,3-diamine, propane-1,2-diamine, butane-1,4-diamine, pentane-1,5-diamine, and o-phenylene diamine. In various aspects, the pH responsive dendrimer repeat unit has a structure according to the following formula

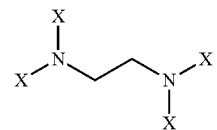

wherein each X is independently a branched acrylate arm having from 2 to 6 acrylate groups and having 2 to 20 carbon atoms. For example, in some aspects, each X is independently selected from the group consisting of trimethylpropane triacrylate, trimethylpropane ethoxylate triacrylate, glycerol triacrylate, glycerol ethoxylate triacrylate, and other small molecule branched acrylates. In one or more aspects, the pH responsive dendrimer repeat unit has a structure according to the following formula or a derivative thereof:

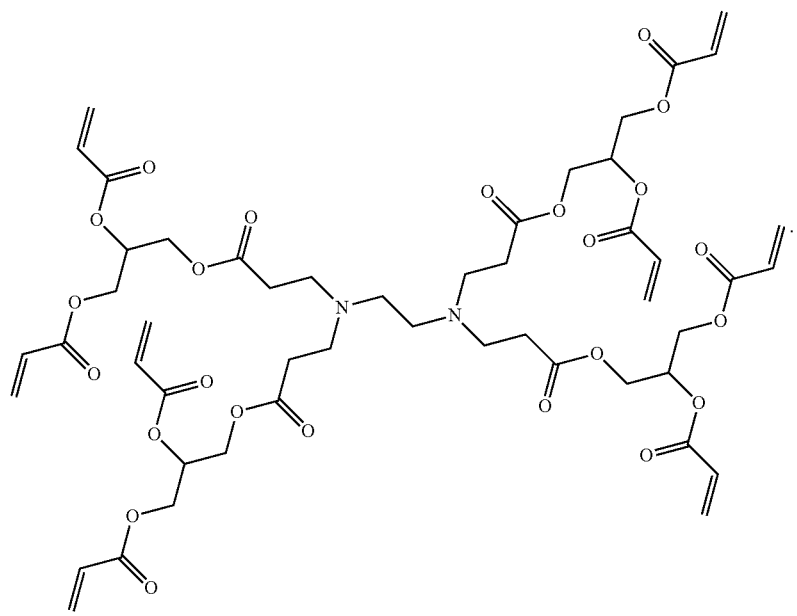

The pH responsive dendrimer repeat unit can have a structure according to the following formula or a derivative thereof

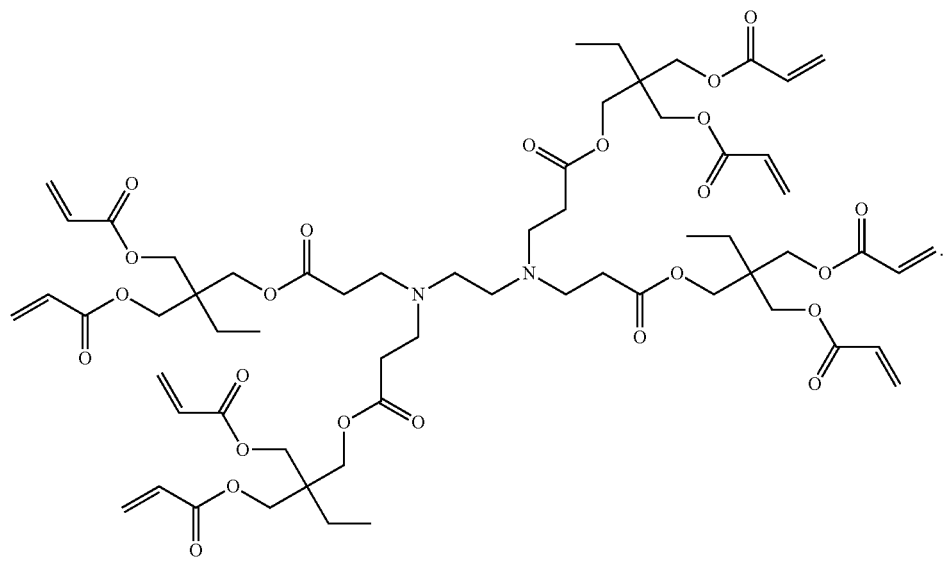

In various aspects, methods of making nanoparticles and compositions thereof are provided. The methods can include forming an oil phase comprising a hydrophobic monomer, a pH responsive dendrimer, and an active agent; adding the oil phase to an aqueous phase to form an emulsion; and polymerizing the hydrophobic monomer and the pH responsive dendrimer to form the nanoparticle having a hydrophobic core comprising the hydrophobic active agent. In various aspects, the hydrophobic monomer and the pH responsive dendrimer can be polymerized by the addition of heat, light, or a catalyst to the emulsion.

A variety of packaged food products are also provided containing a food product; a packaging containing the food product; and a composition comprising a plurality of one or more nanoparticles provided herein. In various aspects, the food product is beef, pork, poultry, or fish. In one or more aspects, the packaged food product is a ready-to-eat food product. In various aspects, the composition containing the nanoparticles is part of the packaging and/or is in contact with the food product inside the packaging. The hydrophobic active agent in the packaged food product can be released from the nanoparticles at the initiation of spoilage of the food product. In one or more aspects, the nanoparticles are chemically stable and have an average diameter of about 50 nm to 200 nm at neutral pH, and then the nanoparticles release the hydrophobic active agent at a pH range of about 4.5 to 6.7 to indicate spoilage of the food product. In various aspects, the release of the hydrophobic active agent indicates the food has spoiled, inhibits or prevents the growth of a food spoilage microorganism, or both.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
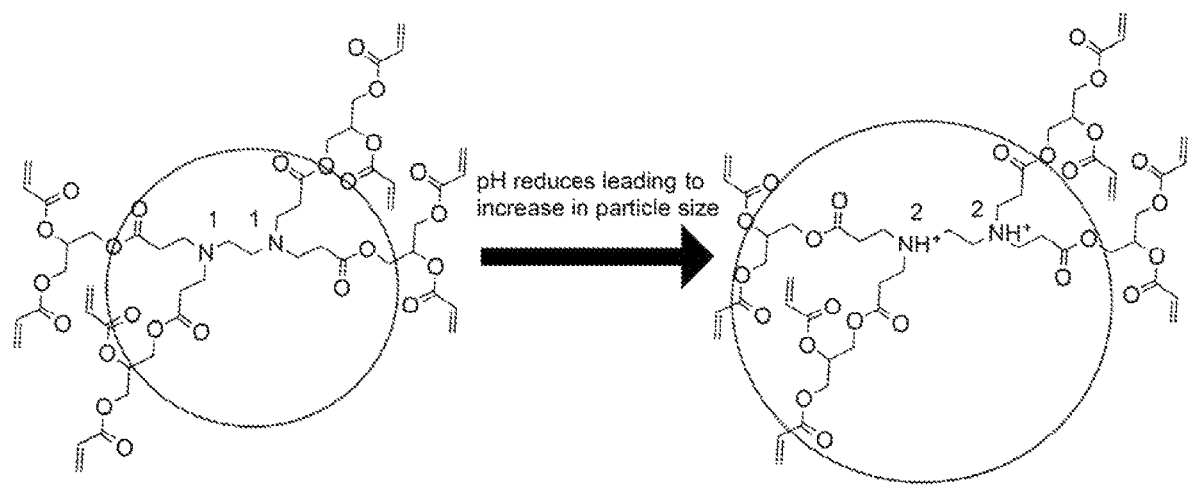
FIG. 1 is a schematic representation of a pH-sensitive dendrimer demonstrating one way a decreasing pH can lead to increased particle size and controlled release of agents contained therein.

Nanoparticles are provided containing a polymer having pH responsive dendrimer repeat units. The nanoparticles can have a hydrophobic core containing one or more hydrophobic active agents. The active agent can be any hydrophobic active agent, for example a hydrophobic dye indicating a condition of food spoilage, a hydrophobic antimicrobial agent that eradicates or prevents the outgrowth of one or more bacteria, or both. The nanoparticles contain pH responsive dendrimers that can include pH responsive crosslinking groups.

Compositions are also provided containing the nanoparticles. The compositions can be a polymer film, a suspension, or a gel. The compositions can be a gel or a suspension reinforced by a microporous fabric. The compositions can contain an effective amount of the nanoparticles to detect and/or prevent the outgrowth of one or more spoilage microorganisms. In particular, the compositions can contain an effect amount of the nanoparticles to detect and/or prevent the outgrowth of one or more spoilage microorganisms in a food product in which the compositions are in contact.

Methods of making the nanoparticles and compositions thereof are provided. The methods can include synthesis of a branched polyol and crosslinking of the polyol by a pH responsive cross-linking group to form a pH responsive dendrimer. The methods can include miniemulsion polymerization of a pH responsive dendrimer and another polymer repeat unit, for example a hydrophobic polymer repeat unit to form the nanoparticles encapsulating a hydrophobic active agent.

Methods of using the nanoparticles and compositions thereof are also provided. The methods can include placing an effective amount of the nanoparticles or a composition thereof in contact with a food product to detect and/or prevent the outgrowth of one of more spoilage microorganisms. The methods can include incorporating the nanoparticles or a composition thereof into the packaging of a food product. The methods can include simply placing compositions containing the nanoparticles inside the packaging with the food product. Packaged food products are provided containing an effective amount of the nanoparticles or compositions thereof. The packaged food products can be packaged meat products.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting. The skilled artisan will recognize many variants and adaptations of the embodiments described herein. These variants and adaptations are intended to be included in the teachings of this disclosure and to be encompassed by the claims herein.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be constructed as an admission that the present disclosure is not entitled to antedate such publication by virtue of prior disclosure. Further, the dates of publication provided could be different from the actual publication dates that may need to be independently confirmed.

Although any methods and materials similar or equivalent to those described herein can also be used in the practice or testing of the present disclosure, the preferred methods and materials are now described. Functions or constructions well-known in the art may not be described in detail for brevity and/or clarity. Embodiments of the present disclosure will employ, unless otherwise indicated, techniques of nanotechnology, organic chemistry, material science and engineering and the like, which are within the skill of the art. Such techniques are explained fully in the literature.

It should be noted that ratios, concentrations, amounts, and other numerical data can be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. Where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In some embodiments, the term "about" can include traditional rounding according to significant figures of the numerical value. In addition, the phrase "about 'x' to 'y'" includes "about 'x' to about 'y'".

Definitions

Unless defined otherwise, all technical and scientific terms used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

The term "small molecule", as used herein, generally refers to an organic molecule that is less than about 2,000 g/mol in molecular weight, less than about 1,500 g/mol, less than about 1,000 g/mol, less than about 800 g/mol, or less than about 500 g/mol. Small molecules are non-polymeric and/or non-oligomeric.

The term "polymer", as used herein, is used as generally understood in the literature and refers to a macromolecule made from many repeat units covalently bonded together. The polymer can be a "homopolymer" meaning it is made entirely of one type of repeat unit, optionally having different end-groups, including capped or acidic end groups. The polymer can be a "copolymer", meaning a single polymeric material that is comprised of two or more different types of monomers.

The copolymer can be of any form, including random, block, and graft copolymers. The copolymers can have any end-group, including capped or acid end groups. The polymer can be linear or branched. The polymer can be characterized by a degree of polymerization that can be either a number-averaged degree of polymerization or a weight-average degree of polymerization. The polymer can have a degree of polymerization that is on the order of 100, 1,000, or even 10,000; for example the polymer can have a degree of polymerization that is about 50, 100, 150, 200, 250, 500, 750, 1,000, 1,500, 2,000, 3,000, 4,000, 5,000, 10,000 or greater. The polymer can have a degree of polymerization that is up to about 80,000, 60,000, 50,000, 40,000, 30,000, 25,000, 20,000, or less. The polymer can be characterized by an average molecular weight, e.g. a weight-averaged molecular weight or a number-average molecular weight. The polymer can have a variety of molecular weights depending upon the size of the repeat units and the degree of polymerization. The polymer can have a molecular weight of about 500 g/mol to 10,000,000 g/mol, about 800 g/mol to 1,000,000 g/mol, about 1,000 g/mol to 1,000,000 g/mol, about 2,000 g/mol to 1,000,000 g/mol, about 2,000 g/mol to 500,000 g/mol, about 2,000 g/mol to 250,000 g/mol, about 2,000 g/mol to 200,000 g/mol, about 2,000 g/mol to 100,000 g/mol, or about 5,000 g/mol to 50,000 g/mol.

The term "oligomer", as used herein, refers to a larger molecule formed from more than one repeat unit covalently bonded in a manner analogous to a polymer but that is still not large enough to be considered a polymer. Oligomers will typically have from a few to tens of repeat units, for example about 2, 3, 4, 5, 6, 7, 8, 9, 10, or more repeat units. Oligomers can have about 80, 60, 50, 40, 30, 25, 20, 18, 17, 16, 15, or fewer repeat units. The oligomer can have a molecular weight from The term "dendrimer", as used herein, refers to a larger molecule or oligomer having a highly branched structure of 1, 2, 3, 4, or more branched arms extending from and attached to, either directly or through a linking moiety, one or more chemically addressable cores. A dendrimer can be symmetric around the core, and can adopt a spherical three-dimensional morphology. The dendrimer can be monodisperse. The dendrimer can be characterized by the "generation", referring to the number of layers or successive branches extending from the core to the surface along an arm of the dendrimer. The dendrimer can have a generation of 1, 2, 3, 4, 5, 6, or more. For a dendrimer synthesized via regular, sequential addition of branched layers, the generation can refer to the number of distinct addition steps. The term dendrimer can include a "dendron", meaning a dendrimer having branches emanating from a single core, either directly or through a linking moiety, to form a dendrimer.

The term "monodisperse", as used herein, refers to a population of particles (e.g., oligomers, dendrimers, or polymers) wherein the particles have substantially identical size and shape. A "monodisperse" population of particles can mean that at least about 60%, 70%, 80%, 90%, 95%, 99%, 99.5%, or more of the particles fall within a specified particle size range that is within plus or minus about 25%, 20%, 15%, 10%, 5%, 3%, 2%, 1%, or less of the root-mean-square (rms) size of the particles in the population.

The term "molecular weight", as used herein, generally refers to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

The terms "active agent", as used herein, includes, without limitation, substances that act to detect, prevent, inhibit, or otherwise slow the progression of spoilage or of a food spoilage microorganism when applied to a surface or to a substance such as a food product.

The term "antimicrobial agent", as sued herein, refers to an agent destroys, inhibits or prevents the propagation, growth and multiplication of unwanted microbial organisms.

The term "microbial organisms" or "microbes" includes, but is not limited to, microorganisms, bacteria, undulating bacteria, spirochetes, spores, spore-forming organisms, gram-negative organisms, gram-positive organisms, yeasts, fungi, molds, viruses, aerobic organisms, anaerobic organisms and mycobacteria. Non-limiting examples of microbial organisms that can be controlled using the formulations and methods described herein include bacteria from the genus *Aeromonas* (e.g. *A. hydrophilia*), Arcobacter, *Bacillus* (e.g. *B. cereus*), Brochothrix (e.g. *B. thermosphacta*), *Campylobacter* (e.g. *C. jejuni*), Carnobacterium (e.g. *C. piscicola*), *Clostridium* (e.g. *C. perfringens, C botulinum*), Enterobacteriacae, *Escherichia* (e.g. *E. coli* O157:H7), *Listeria* (e.g. *L. monocytogenes*), *Pseudomonas* (e.g. *P. putida, P. fluorescens*), *Salmonella* (e.g. *S. Typhimurium*), *Serratia* (e.g. *S. liquefaciens*), *Shigella, Staphylococcus* (e.g. *S. aureus*), *Vibrio* (e.g. *V. parahaemolyticus, V. cholerae*) and *Yersinia* (e.g. *Y. enterocolitica*); fungi such as *Aspergillus* flavum and *Penicillium chrysogenum*; parasites such as *Entamoeba* (*Entamoeba histolytica*), *Balantidium* (*Balantidium* cob), *Cryptosporidium* (e.g. *Cryptosporidium parvum*), *Cyclospora* (e.g. *Cyclospora cayetanensis*), *Giardia* (e.g. *Giardia lamblia, Giardia intestinalis*), *Isospora* (*Isospora* belle), Microsporidia (*Enterocytozoon bieneusi, Septata intestinalis*), *Trichinella spiralis* and *Toxoplasma gondii*. The term microbial organism also refers to vegetative or dormant forms of bacteria and fungi, such as spores wherein activation of the growth cycle may be controlled using the methods provided herein.

The terms "spoilage micro-organism" and "spoilage microbial organism", as used interchangeably herein refer to a micro-organism that acts to spoil food. Spoilage micro-organisms may grow and proliferate to such a degree that a food product is made unsuitable or undesirable for human or animal consumption. The production of undesirable by-products by the microorganism, such as carbon dioxide, methane, nitrogenous compounds, butyric acid, propionic acid, lactic acid, formic acid, sulfur compounds, and other gases and acids can cause detrimental effects on the foodstuff alteration of the color of meat surfaces to a brown, grey or green color, or creation of an undesirable odor. The color and odor alterations of food products due to the growth of spoilage micro-organisms frequently result in the product becoming unfit for sale or consumption.

The term "pathogenic micro-organism" as used herein refers to a micro-organism capable of causing disease or illness in an animal or a human, for example, by the production of endotoxins, or by the presence of a threshold level of micro-organisms to cause food poisoning, or other undesirable physiological reactions in humans or animals.

The term "derivative" refers to any compound having the same or a similar core structure to the compound but having at least one structural difference, including substituting, deleting, and/or adding one or more atoms or functional groups. The term "derivative" does not mean that the derivative is synthesized from the parent compound either as a starting material or intermediate, although this may be the case. The term "derivative" can include salts, prodrugs, or metabolites of the parent compound. Derivatives include compounds in which free amino groups in the parent compound have been derivatized to form amine hydrochlorides, p-toluene sulfoamides, benzoxycarboamides, t-butyloxycarboamides, thiourethane-type derivatives, trifluoroacetylamides, chloroacetylamides, or formamides. Derivatives include compounds in which carboxyl groups in the parent compound have been derivatized to form salts, methyl and ethyl esters or other types of esters or hydrazides. Derivatives include compounds in which hydroxyl groups in the parent compound have been derivatized to form O-acyl or O-alkyl derivatives. Derivatives include compounds in which a hydrogen bond donating group in the parent compound is replaced with another hydrogen bond donating group such as OH, NH, or SH. Derivatives include replacing a hydrogen bond acceptor group in the parent compound with another hydrogen bond acceptor group such as esters, ethers, ketones, carbonates, tertiary amines, imine, thiones, sulfones, tertiary amides, and sulfides.

The terms "biocompatible" and "biologically compatible", as used interchangeably herein, refer to materials that are, with any metabolites or degradation products thereof, generally non-toxic to the recipient, and cause no significant adverse effects to the recipient. Generally speaking, biocompatible materials are materials which do not elicit a significant inflammatory or immune response when administered to a patient. In some embodiments a biocompatible material elicits no detectable change in one or more biomarkers indicative of an immune response. In some embodiments, a biocompatible material elicits no greater than a 10% change, no greater than a 20% change, or no greater than a 40% change in one or more biomarkers indicative of an immune response.

The terms "sufficient" and "effective", as used interchangeably herein, refer to an amount (e.g. mass, volume, dosage, concentration, and/or time period) needed to achieve one or more desired result(s). For example, a diagnostically effective amount refers to an amount needed to achieve one or more diagnostic effects or to indicate the occurrence of a diagnostic criteria.

Biodegradable polymers can include polymers that are insoluble or sparingly soluble in water that are converted chemically or enzymatically in the body into water-soluble materials. Biodegradable polymers can include soluble polymers crosslinked by hydrolyzable cross-linking groups to render the crosslinked polymer insoluble or sparingly soluble in water. Biodegradable polymers in the conjugate can include polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexylmethacrylate), poly(isodecylmethacrylate), poly(lauryl methacrylate), poly (phenyl methacrylate), poly(methyl acrylate), poly(isopropyl acrylate), poly(isobutyl acrylate), poly(octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene and polyvinylpyrrolidone, derivatives thereof, linear and branched copolymers and block copolymers thereof, and blends thereof.

The term "food products", as used herein, is to be understood in a broad sense and includes meat products, fish products, dairy products, beverage products, baking products, unpasteurized food products, salads, and sauces, marinades, salsas and seasonings. In some embodiments, the food product contains one or more meat products such as beef, pork, poultry, or fish. The food products can be ready-to-eat food products. The term "ready-to-eat" means the food product is distributed to be consumed without further preparation by the consumer or distributed to not require cooking or preparation to achieve food safety prior to consumption.

The term "meat product", as used herein, includes any food product that primarily contains animal tissue, e.g. contains at least 70%, at least 80%, at least 90%, or at least 95% animal tissue including, but not limited to, beef, pork, poultry, and fish. Other animal tissues can include the tissue of many ungulates that can be used for human consumption such as deer, oxen, antelope, sheep, and goat. The term "meat product" as used herein encompasses processed meats (such as sausages, hamburgers, luncheon meats and cold cuts) and pre-prepared meat dishes such as meat pies, fish pies, game pies, stews, lasagnas and other meat-containing pasta dishes, chicken kiev, chicken cordon-bleu, chicken-a-la-king, meat rolls, meatloaf, pates, sushi, sashimi, salmon mousses, fishcakes, stir-fries etc. The term "ready-to-eat meat product" should include any meat product, which is distributed to be consumed without further preparation by the consumer or distributed to not require cooking prior to consumption. Ready-to-eat meat products include, but are not limited to, pates, hot dogs, bologna, ham, salami, sausages, deli meats, cold cuts, and dried or cured meat products. Ready-to-eat meat products can include ready-to-eat beef products, ready-to-eat pork products, ready-to-eat poultry products, and ready-to-eat fish products.

The term "beef product", as used herein, refers to any food that primarily contains cow tissue, e.g. contains at least 70%, at least 80%, at least 90%, or at least 95% cow tissue. The term "cow" refers to any animal of the genus *Bos*, such as for example the *Bos Taurus*, which is used as a food source for human consumption. Exemplary cow breeds used as commercial livestock include the Holstein, Ayrshire, Angus, and Limousin.

The term "poultry product", as used herein, refers to any food that primarily contains poultry tissue, e.g. contains at least 70%, at least 80%, at least 90%, or at least 95% poultry tissue. The term "poultry" refers to any edible birds such as chickens, turkeys, ducks, geese, and squab. Poultry can include animals of the genus *Gallus*, for example the *Gallus gallus domesticus*, which is used as a food source for human consumption. Poultry can include animals of the genus *Meleagris*, for example the *Meleagris gallopavo*, which is used as a food source for human consumption.

The term "pork product", as used herein, refers to any food product that primarily contains pig tissue, e.g. contains at least 70%, at least 80%, at least 90%, or at least 95% pig tissue. The term "pig" refers to any animal of the genus *Sus*, such as for example *Sus scrofa*, which is used as a food source for human consumption. Exemplary pig breeds used as commercial livestock include Berkshire, Large White, Duroc, Hampshire, Landrace, Meishan, Pietrain, and many others.

As used herein, the term "fish product" should include any food product that primarily contains tissue from an aquatic animal, e.g. contains at least 70%, at least 80%, at least 90%, or at least 95% tissue from an aquatic animal. Aquatic animals can include lobster, crab, fresh water fish, smoked salmon, smoked other fish, salted fish, saltwater fish and other seafood.

As used herein, the term "dairy product" should include any food product made using milk or milk products, including, but not limited to, milk, yogurt, ice cream, cheese, skimmed milk, acidified milk, butter milk, condensed milk, spreads, margarines, milk powder, butter, EMC (Enzyme Modified Cheese), dulce de leche, coffee whitener; coffee creamer, cream, sour cream, ghee, and dairy analogue. Cheese may be any cheese, e.g. fresh cheese, hard cheese, curd cheese, cream cheese, white mold cheese, blue mold cheese and processed cheese.

As used herein, the term "unpasteurized food product" should include any food product, whereby at least one ingredient is unpasteurized and which undergoes no final heat treatment.

As used herein, an "effective amount" is at least the minimum concentration required to have the desired effect, e.g. the minimum concentration required to indicate the presence of a detectable level of one or more microorganisms or the minimum concentration required to cause a measurable decrease in the growth rate of one of more microorganisms or a measurable decrease in the amount of one or more microorganisms. An effective amount can substantially prevent the growth of one or more microorganisms for a period of time up to about 5 days, 7 days, 10 days, 14 days, 21 days, 25 days, 30 days, or 45 days.

The term "safe", as used herein with reference to food, refers to a state wherein the food is sufficiently free of pathogenic micro-organisms or the toxic products of microbial growth to be fit for human or animal consumption.

As used herein, the term "shelf life" refers to the period of time that a food product remains saleable to retail customers and remains fit and safe for use or consumption. Changes including, but not limited to, oxidation, odor development, discoloration in addition to microbial changes can alter the shelf life of the food product. In traditional meat processing, the shelf life of fresh meat and meat by-products is about 30 to 40 days after an animal has been slaughtered. Refrigeration of meat during this period of time largely arrests and/or retards the growth of microorganisms. Microorganisms present on meat products may have proliferated to a great extent and/or have generated unacceptable levels of undesirable by-products. Spoilage microorganisms may also act to discolor meat, making such meat unappealing and undesirable for human consumption. Pathogenic microorganisms may have proliferated in this time period to a level wherein they can cause disease in an animal that consumes the food product.

As used herein, the term "usable life" refers to the period of time that a high-pressure processed food product remains fit for human consumption, e.g. safe and substantially free of food spoilage, after having been removed from the original packaging. For example, deli-style ready-to-eat meat products may be opened and sliced at the deli counter. The unsliced meat at the deli counter will have a usable life different from the sliced deli meat. The usable life will depend upon factors such as the storage temperature, the surface area, and the handling conditions.

"Food spoilage", as used herein, refers to organoleptic changes in the food, i.e. alterations in the condition of food which makes it less palatable, for example, changes in taste, smell, texture or appearance which are related to contamination of the food with one or more spoilage microorganisms. Spoiled food may or may not be safe for consumption.

"Food preservation", as used herein, refers to methods which maintain or enhance food safety for example, by controlling the growth and proliferation of pathogenic and spoilage micro-organisms, thus guarding against food poisoning and delaying or preventing food spoilage. Food preservation helps food remain safe for consumption for longer periods of time (i.e. improves the shelf life) and inhibits or prevents nutrient deterioration and/or organoleptic changes which cause food to become less palatable.

The term "neutral pH," as used herein refers to a pH of about 6.8 to 7.2, about 6.9 to 7.1, about 6.95 to 7.05, or about 7.0.

The term "chemical stability", as generally used herein, refers to the ability of the nanoparticles to resist degradation via chemical pathways, such as oxidation, deamidation, or hydrolysis and/or to contain the contents of the nanoparticle for an extended period without substantially releasing the contents. A nanoparticle formulation is typically considered chemically stable if about 25%, 20%, 15%, 10%, 5%, or less of the components are degraded or if less than about 25%, 20%, 15%, 10%, 5%, or 1% of the contents of the nanoparticle are released after 1, 2, 3, 6, 9, 12, 24 months at about room temperature, e.g. about 20° C. to 25° C.

The term "alkyl" refers to the radical of saturated aliphatic groups (i.e., an alkane with one hydrogen atom removed), including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, and $C_3$-$C_{30}$ for branched chains), preferably 20 or fewer, more preferably 15 or fewer, most preferably 10 or fewer. Likewise, preferred cycloalkyls have 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

The term "heteroalkyl", as used herein, refers to straight or branched chain, or cyclic carbon-containing radicals, or combinations thereof, containing at least one heteroatom. Suitable heteroatoms include, but are not limited to, O, N, Si, P, Se, B, and S, wherein the phosphorous and sulfur atoms are optionally oxidized, and the nitrogen heteroatom is optionally quaternized. Heteroalkyls can be substituted as defined above for alkyl groups.

The term "alkylthio" refers to an alkyl group, as defined above, having a sulfur radical attached thereto. In preferred embodiments, the "alkylthio" moiety is represented by one of —S— alkyl, —S-alkenyl, and —S-alkynyl. Representative alkylthio groups include methylthio, ethylthio, and the like. The term "alkylthio" also encompasses cycloalkyl groups, alkene and cycloalkene groups, and alkyne groups.

"Arylthio" refers to aryl or heteroaryl groups. Alkylthio groups can be substituted as defined above for alkyl groups.

The terms "alkenyl" and "alkynyl", refer to unsaturated aliphatic groups analogous in length and possible substitution to the alkyls described above, but that contain at least one double or triple bond respectively.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, and —O-alkynyl. The terms "aroxy" and "aryloxy", as used interchangeably herein, can be represented by —O-aryl or O-heteroaryl, wherein aryl and heteroaryl are as defined below. The alkoxy and aroxy groups can be substituted as described above for alkyl.

The terms "amine" and "amino" (and its protonated form) are art-recognized and refer to both unsubstituted and substituted amines, e.g., a moiety that can be represented by the general formula:

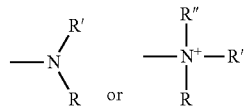

wherein R, R', and R" each independently represent a hydrogen, an alkyl, an alkenyl, —$(CH_2)_m$—$R_c$ or R and R' taken together with the N atom to which they are attached complete a heterocycle having from 4 to 8 atoms in the ring structure; $R_c$ represents an aryl, a cycloalkyl, a cycloalkenyl, a heterocycle or a polycycle; and m is zero or an integer in the range of 1 to 8. In preferred embodiments, only one of R or R' can be a carbonyl, e.g., R, R' and the nitrogen together do not form an imide. In still more preferred embodiments, the term "amine" does not encompass amides, e.g., wherein one of R and R' represents a carbonyl. In even more preferred embodiments, R and R' (and optionally R") each independently represent a hydrogen, an alkyl or cycloalkyl, an alkenyl or cycloalkenyl, or alkynyl. Thus, the term "alkylamine" as used herein means an amine group, as defined above, having a substituted (as described above for alkyl) or unsubstituted alkyl attached thereto, i.e., at least one of R and R' is an alkyl group.

The term "amido" is art-recognized as an amino-substituted carbonyl and includes a moiety that can be represented by the general formula:

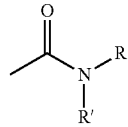

wherein R and R' are as defined above.

"Aryl", as used herein, refers to $C_5$-$C_{10}$-membered aromatic, heterocyclic, fused aromatic, fused heterocyclic, biaromatic, or biheteroocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine, pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN, and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3 b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. One or more of the rings can be substituted as defined above for "aryl".

The term "aralkyl", as used herein, refers to an alkyl group substituted with an aryl group (e.g., an aromatic or heteroaromatic group).

The term "aralkyloxy" can be represented by —O-aralkyl, wherein aralkyl is as defined above.

The term "carbocycle", as used herein, refers to an aromatic or non-aromatic ring(s) in which each atom of the ring(s) is carbon.

"Heterocycle" or "heterocyclic", as used herein, refers to a monocyclic or bicyclic structure containing 3-10 ring atoms, and preferably from 5-6 ring atoms, consisting of carbon and one to four heteroatoms each selected from the group consisting of non-peroxide oxygen, sulfur, and N(Y) wherein Y is absent or is H, O, ($C_1$-$C_{10}$) alkyl, phenyl or benzyl, and optionally containing 1-3 double bonds and optionally substituted with one or more substituents. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxepanyl, oxetanyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydropyranyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, and xanthenyl. Heterocyclic groups can optionally be substituted with one or more substituents at one or more positions as defined above for alkyl and aryl, for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocycle, an aromatic or heteroaromatic moiety, —$CF_3$, —CN, or the like.

The term "carbonyl" is art-recognized and includes such moieties as can be represented by the general formula:

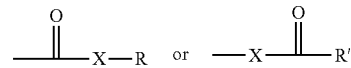

wherein X is a bond or represents an oxygen or a sulfur, and R and R' are as defined above. Where X is an oxygen and R or R' is not hydrogen, the formula represents an "ester". Where X is an oxygen and R is as defined above, the moiety is referred to herein as a carboxyl group, and particularly when R is a hydrogen, the formula represents a "carboxylic acid". Where X is an oxygen and R' is hydrogen, the formula represents a "formate". In general, where the oxygen atom of the above formula is replaced by sulfur, the formula represents a "thiocarbonyl" group. Where X is a sulfur and R or R' is not hydrogen, the formula represents a "thioester." Where X is a sulfur and R is hydrogen, the formula represents a "thiocarboxylic acid." Where X is a sulfur and R' is hydrogen, the formula represents a "thioformate." On the other hand, where X is a bond, and R is not hydrogen, the above formula represents a "ketone" group. Where X is a bond, and R is hydrogen, the above formula represents an "aldehyde" group.

The term "heteroatom" as used herein means an atom of any element other than carbon or hydrogen. Preferred heteroatoms are boron, nitrogen, oxygen, phosphorus, sulfur, and selenium. Other heteroatoms include silicon and arsenic.

As used herein, the term "nitro" means —$NO_2$; the term "halogen" designates —F, —Cl, —Br, or —I; the term "sulfhydryl" means —SH; the term "hydroxyl" means —OH; and the term "sulfonyl" means —SO₂—.

The term "substituted" as used herein, refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl groups, or any other organic groupings containing any number of carbon atoms, preferably 1-14 carbon atoms, and optionally include one or more heteroatoms such as oxygen, sulfur, or nitrogen grouping in linear, branched, or cyclic structural formats. Representative substituents include alkyl, substituted alkyl, alkenyl, substituted alkenyl, alkynyl, substituted alkynyl, phenyl, substituted phenyl, aryl, substituted aryl, heteroaryl, substituted heteroaryl, halo, hydroxyl, alkoxy, substituted alkoxy, phenoxy, substituted phenoxy, aroxy, substituted aroxy, alkylthio, substituted alkylthio, phenylthio, substituted phenylthio, arylthio, substituted arylthio, cyano, isocyano, substituted isocyano, carbonyl, substituted carbonyl, carboxyl, substituted carboxyl, amino, substituted amino, amido, substituted amido, sulfonyl, substituted sulfonyl, sulfonic acid, phosphoryl, substituted phosphoryl, phosphonyl, substituted phosphonyl, polyaryl, substituted polyaryl, $C_3$-$C_{20}$ cyclic, substituted $C_3$-$C_{20}$ cyclic, heterocyclic, substituted heterocyclic, amino acid, peptide, and polypeptide groups.

Heteroatoms such as nitrogen may have hydrogen substituents and/or any permissible substituents of organic compounds described herein which satisfy the valences of the heteroatoms. It is understood that "substitution" or "substituted" includes the implicit proviso that such substitution is in accordance with permitted valence of the substituted atom and the substituent, and that the substitution results in a stable compound, i.e., a compound that does not spontaneously undergo transformation such as by rearrangement, cyclization, elimination, etc.

Nanoparticles

Nanoparticles and compositions containing a plurality of the nanoparticles are provided. The nanoparticles can have a hydrophobic core containing one or more hydrophobic active agents. The nanoparticles can also contain a copolymer of a hydrophobic polymer repeat unit and a pH responsive dendrimer repeat unit. The nanoparticles can have a diameter, or the plurality of nanoparticles can have an average diameter, that is from about 50 nm to 500 nm, from about 50 nm to 250 nm, or from about 100 nm to 250 nm at a neutral pH. The nanoparticles can be useful to release the hydrophobic active agent a specific pH while maintaining stability and integrity at an elevated pH. The nanoparticles can therefore be useful in a variety of contexts to deliver an active agent in response to a change in pH, for example in the monitoring and preventing of food spoilage. The nanoparticles can be biocompatible and or safe for human consumption.

The nanoparticles can have a variety of sizes adapted to the particular needs. The nanoparticles can have a diameter of about 10 nm to 1000 nm, about 20 nm to 1000 nm, about 20 nm to 900 nm, about 20 nm to 800 nm, about 30 nm to 800 nm, about 30 nm to 750 nm, about 40 nm to 750 nm, about 50 nm to 750 nm, about 50 nm to 700 nm, about 50 nm to 650 nm, about 50 nm to 600 nm, about 50 nm to 550 nm, or about 50 nm to 500 nm. In some embodiments of plurality of nanoparticles are provided in a composition, the plurality of nanoparticles having an average diameter of about 10 nm to 1000 nm, about 20 nm to 1000 nm, about 20 nm to 900 nm, about 20 nm to 800 nm, about 30 nm to 800 nm, about 30 nm to 750 nm, about 40 nm to 750 nm, about 50 nm to 750 nm, about 50 nm to 700 nm, about 50 nm to 650 nm, about 50 nm to 600 nm, about 50 nm to 550 nm, or about 50 nm to 500 nm. The plurality of nanoparticles can be monodisperse.

The nanoparticles can be used to deliver or release the active agent(s) in response to a change in the pH. The nanoparticles can release the active agent(s) as a function of changes in the pH. In some embodiments the nanoparticles release the active agent(s) in response to changes in the pH associated with food spoilage. The pH associated with food spoilage, e.g. at which the nanoparticles release the active agent(s), can be about 6.8, 6.7, 6.6, 6.5, 6.4, 6.3, 6.2, 6.1, 6.0, 5.9, 5.8, 5.7, 5.6, or less. In some embodiments the nanoparticles release the active agent(s) over a pH range of about 4 to 7, about 4.5 to 7, about 5 to 7, about 5 to 6.8, about 5.5 to 6.8, about 5.6 to 6.8, about 5.6 to 6.7, about 5.6 to 6.6, about 5.8 to 6.6, or about 6.0 to 6.6.

pH Responsive Dendrimer

The nanoparticle can include a pH responsive dendrimer. A variety of pH responsive dendrimers can be used. The pH responsive dendrimer can have a pH responsive amine core and a branched acrylate arm. The pH responsive amine core can change shape, size, and/or confirmation is response to a change in the pH. For example, protonation of the amines on the amine core can induce structural changes in the pH responsive amine core that induce structural changes in the arms of the dendrimer.

The pH responsive dendrimer can include a pH responsive amine core. The pH responsive amine core can be any substituted or unsubstituted, linear or branched alkyl amine having two or more amine group and having from about 2 to 20, 2 to 12, 2 to 10, 2 to 8, or 2 to 6 carbon atoms. The pH responsive amine core can be a polyamine, e.g. a diamine, a triamine, or a tetramine. The pH responsive amine core can be a diamine such as ethylene diamine, propane-1,3-diamine, propane-1,2-diamine, butane-1,4-diamine, pentane-1,5-diamine, or o-phenylene diamine. In some embodiments the pH responsive amine core is ethylene diamine.

The pH responsive amine core can have a structure defined by the formula

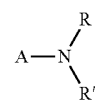

where A is a substituted or unsubstituted, linear or branched alkyl, heteroalkyl, alkenyl, alkynyl, carbocyclic, or heterocyclic group, preferably having about 1 to 20, 1 to 15, 1 to 12, 2 to 12, 2 to 10, 2 to 8, 2 to 6, or 2 to 5 carbon atoms; and where n is an integer greater than 2, preferably from 2 to 10, 2 to 8, 2 to 6, 2 to 5, 2 to 4, 2 to 3, or wherein n is 2. R and R' can be as defined above. In some aspects, R and/or R' include an acrylate arm as described more specifically below.

The pH responsive dendrimer can include a branched acrylate arm. The branched acrylate arm can include any acrylate structure, preferably having about 6 to 30, about 6 to 25, about 8 to 25, about 8 to 20, about 10 to 20, about 10 to 15, or about 12 carbon atoms. The pH responsive dendrimer can be an acrylate formed by the esterification of acryloyl chloride with a polyol. The polyol can be, for example, ethylene glycol, propylene glycol, glycerol, 1,2-butanediol, 1,3-butanediol, pentaerythritol, maltitol, sorbitol, or other small molecule polyol. The acrylate can have a structure according the formula

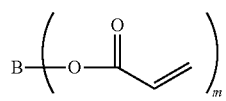

where B is a substituted or unsubstituted, linear or branched alkyl, heteroalkyl, alkenyl, alkynyl, carbocyclic, or heterocyclic group, preferably having about 1 to 20, 1 to 15, 1 to 12, 2 to 12, 2 to 10, 2 to 8, 2 to 6, or 2 to 5 carbon atoms; and where m is an integer greater than 2, preferably from 2 to 10, 2 to 8, 3 to 8, 3 to 6, 3 to 5, 3 to 4, or wherein n is 3.

The pH responsive dendrimer can have an tertiary amine core having branched acrylate arms attached thereto. For example, the pH responsive dendrimer can have a structure according to the formula

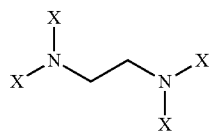

where each X is independently a branched acrylate arm, including any of the branched acrylate structures described herein. For example, each X can be a branched acrylate having from 2 to 6, 2 to 5, 2 to 4, or about 3 acrylate groups and having about 2 to 20, 2 to 12, 3 to 12, or 3 to 8 carbon atoms. In some embodiments each X is independently selected from trimethylpropane triacrylate, trimethylpropane ethoxylate triacrylate, glycerol triacrylate, glycerol ethoxylate triacrylate, and other small molecule branched acrylates.

The pH responsive dendrimer can have a structure according to the formula shown below or a derivative thereof.

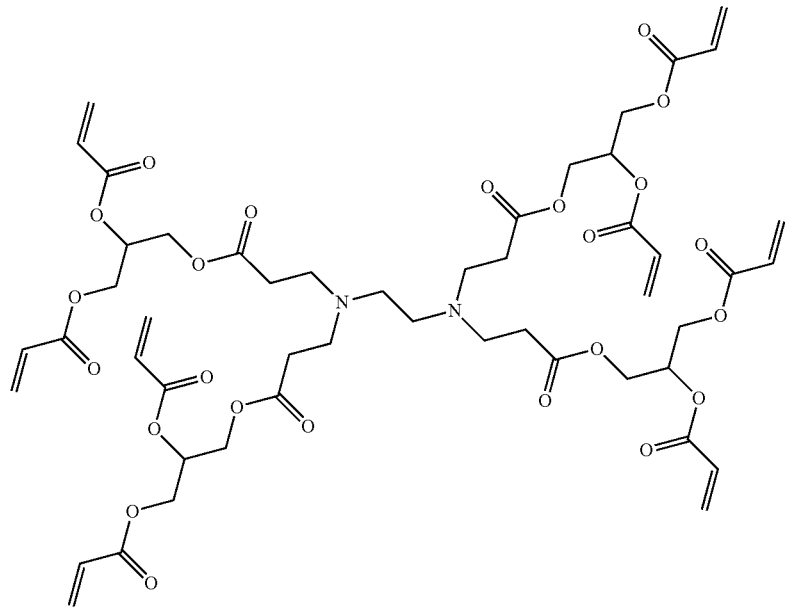 [SMILES: C=CC(=O)OCC(COC(=O)CCN(CCC(=O)OCC(COC(=O)C=C)OC(=O)C=C)CCN(CCC(=O)OCC(COC(=O)C=C)OC(=O)C=C)CCC(=O)OCC(COC(=O)C=C)OC(=O)C=C)OC(=O)C=C]

The pH responsive dendrimer can be a first-generation dendrimer, a second-generation dendrimer, a third-generation dendrimer, or higher. For example, the dendrimer can have a generation from about 1 to 10, about 1 to 8, about 1 to 6, about 1 to 5, or about 1 to 4.

Copolymers

The nanoparticle can include a copolymer of the pH responsive dendrimer with a hydrophobic monomer, i.e. the copolymer can contain pH responsive dendrimer repeat units and hydrophobic polymer repeat units. The copolymers can include additional repeat units. For example, the copolymers can include biodegradable polymer repeat units, hydrophobic polymer repeat units, hydrophilic polymer repeat units, stealth polymer repeat units, or the like. The copolymer can be a block copolymer or a random copolymer. The hydrophobic polymer repeat unit can be a fluorocarbon, a tetrafluoroethylene, a vinylfluoride, a siloxane, a dimethylsiloxane, butadiene, a methacrylate such as methyl methacrylate, ethylene, an olefin, styrene, propylene, or an oligomer thereof, preferably having from about 2 to 30 carbon atoms, 2 to 20 carbon atoms, 2 to 12 carbon atoms, or 2 to 10 carbon atoms. In some embodiments the hydrophobic polymer repeat unit is styrene or a derivative or oligomer thereof.

The ratio of the monomers can be used to adjust the properties such as the chemical and physical stability of the nanoparticle, and physical properties of the composite polymer film (strength and rigidity, temperature and humidity effects, stiffness and flexibility). In some embodiments the ratio (w/w) of the pH responsive dendrimer repeat unit to the hydrophobic monomer repeat unit is about 25:75, 20:80, 15:85, 10:90, or 5:95. For example, the pH responsive dendrimer repeat unit can be about 2% to 30%, about 5% to 25%, about 10% to 20%, or about 15% by weight of the copolymer.

Hydrophobic Active Agents

The nanoparticle can include a hydrophobic active agent. The active agent can be a hydrophobic therapeutic agent, a hydrophobic prophylactic agent, or a hydrophobic diagnostic agent.

The hydrophobic active agent can be a hydrophobic dye. For example, in detecting food spoilage the nanoparticles can release the dye in response to a change in the pH. When the food reaches a pH near the initiation of food spoilage, e.g. a pH of about 6.7, 6.6, 6.5, 6.4, 6.3, 6.2, 6.1, 6.0, 5.9, or 5.8, the nanoparticles can begin to release the dye as an indicator of food spoilage. Hydrophobic dyes can be organic compounds with a maximum extinction coefficient greater than 1000 L/mol/cm in the wavelength range of 400 to 750 nm and that are uncharged in aqueous solution at a pH in the range from 6 to 9. The hydrophobic dyes can be devoid of polar solubilizing groups. In some embodiments, the hydrophobic dye does not contain any sulfonic acid, carboxylic acid, or quaternary ammonium groups. The hydrophobic dye chromophore can contain an azo; methine, pyrazole napthoquinone, phthalocyanine; and, triphenylmethane chromophores. Suitable dyes can include pH indicator dyes such as Bromocresol green, Bromophenol blue, Methyl red, Ethyl orange, Solvent Blue 59, Nile red, and combinations thereof. The dye can be biocompatible and/or safe for human consumption.

The hydrophobic active agent can include a hydrophobic antimicrobial agent. For example, in preventing food spoilage the nanoparticles can release the antimicrobial agent in response to a change in the pH. When the food reaches a pH near the initiation of food spoilage, e.g. a pH of about 6.7, 6.6, 6.5, 6.4, 6.3, 6.2, 6.1, 6.0, 5.9, or 5.8, the nanoparticles can begin to release the antimicrobial agent in an effective amount to slow or prevent the growth of spoilage microorganisms. The antimicrobial agent can be an edible organic acid or a consumable salt thereof. The antimicrobial agent can be an oxidizing agent such as acidified sodium chlorite, chlorine dioxide, per-acid solutions, hydrogen peroxide, chlorine compounds such as hypochlorite, metal hypohalites; quaternary ammonium surfactant compounds; organic carboxylic acids such as GRAS or food grade acids including but not limited to citric acid, lactic acid, malic acid, acetic acid and the like; phenol and cresol compounds; halogens and halogenated compounds such as iodine, iodine liberating compounds and complexes such as iodophors, and compounds having covalently bound iodine, chlorine, bromine, chlorine or bromine liberating compounds and complexes, and compounds having covalently bound chlorine or bromine; natural plant or animal extracts such as grapefruit seed extract and tea tree oil; enzymatic products, surface-active agents, parabens, alcohols, solutions of heavy metals, chlorhexidine, peroxygen compounds, triazines, and aldehydes, and fatty acid monoesters; as well as active derivatives and/or combinations of all of the above. The antimicrobial agent can be released in an effective amount to slow or prevent the outgrowth of a spoilage microorganism.

Compositions

The nanoparticles are provided in a variety of compositions, the properties of which can be tailored to the specific application. The compositions can be in permeable, semi-permeable, or impermeable films, granular solids or powders, sheets, or the like. The compositions can be provided as granular solids or powders and packaged in a permeable or semi-permeable packets to be used for food preservation and/or the detection of spoilage in packaged food products.

Packaged food products are also provided containing an effective amount of the nanoparticle compositions to detect and/or prevent food spoilage. The nanoparticle compositions can be formed into films that are part of the food packaging or that can be incorporated inside the packaging such that they nanoparticles are in fluid contact with the food product. For example, food preservation packets containing the nanoparticle compositions and having a permeable or semi-permeable packaging can be included inside the food packaging with the food product. The compositions can be used to detect and/or prevent food spoilage in a variety of food products. In some embodiments the food product is a ready to eat food product. The food product can be a meat product such as a beef product or a pork product, fish product, dairy product, beverage product, baking product, unpasteurized food product, salad, sauce, marinade, salsa or seasoning. The compositions can substantially prevent the growth of one or more microorganisms for a period of time up to about 5 days, 7 days, 10 days, 14 days, 21 days, 25 days, 30 days, or 45 days. The compositions can increase the shelf life and/or increase the usable life of the food product.

TABLE 1

Comparison of the pH at the initiation of food spoilage and final pH at food spoilage for various meat products.

| Food | pH at initiation of spoilage | Final pH |
| --- | --- | --- |
| Ham | 6.3 | 5.1 |
| Turkey fillet | 6.4 | 5.2 |
| Pork loin | 6 | 5.6 |
| Bacon | 5.9 | 5.8 |
| Turkey breast | 6.4 | 5.3 |
| Sausage | 6.3 | 4.5 |
| Chicken | 6.7 | 5.7 |
| Fresh fish (min. processing) | 6 | 11 |
| Frozen fish | 6 | 5.1 |
| Cooked fish (cod) | 6.6 | 6.6 |
| Beef | 5.8 | 3.9 |

Methods of Making

Methods of making the nanoparticles and nanoparticle compositions are provided. The methods can include miniemulsion polymerization to form the nanoparticles. The methods can include forming an oil phase containing a hydrophobic monomer, a pH responsive dendrimer, and an active agent. The methods can also include adding costabilizers to the oil phase. The methods can include sonication of the oil phase. The methods can include adding the oil phase to a water phase including the emulsifier, optionally including sonication, to form an emulsion.

The methods can include the addition of heat, light, or a catalyst to the emulsion to induce the polymerization to form the nanoparticles. The methods can include forming the emulsion at a first temperature below the polymerization temperature of the monomer and the dendrimer, followed by increasing the temperature to a second temperature above the polymerization temperature to induce the polymerization and form the nanoparticles. The first temperature can be at or around room temperature. The second temperature can be about 70° C. to 80° C., about 72° C. to 68° C., or about 73° C. to 67° C.

The methods can include adding a costabilizer or emulsifier such as modified gum Arabic, lecithin, agar, modified ghatti gum, pectin, Kara gum, xanthan gum, modified starch (especially modified food starch, e.g., modified corn starch), polyoxyethylene sorbitan, polyoxyethylene sorbitol esters (e.g. Polysorbate 20, Polysorbate 80, etc.), sugar esters, fatty alcohols (e.g., stearyl alcohol, palmityl alcohol, hexadecane—stearyl alcohol, etc.), single—and/or di-glycerides, proteins, and combinations thereof. The stabilizer can include hexadecane.

Methods of Using

Methods of using the nanoparticles, nanoparticle compositions, and the packaged food products containing the nanoparticle compositions are provided. The methods can include delivering and/or releasing an active agent in response to a change in the pH. The skilled artisan will recognize a variety of applications where delivery of a hydrophobic active agent in response to a decrease in the pH would be used.

The methods can include detecting, inhibiting, and/or preventing food spoilage. The methods can include placing the nanoparticles or compositions containing the nanoparticles in contact with a food product and visually detecting the presence of the dye in the packaging or on the food product indicating the presence of food spoilage microorganisms or indicating that the food is not safe for human consumption. The methods can include inhibiting or preventing the spoilage of a food product. The methods can include placing the nanoparticles or compositions containing the nanoparticles in contact with a food product, whereby the nanoparticles release an antimicrobial agent at the pH indicative of the onset of food spoilage. The antimicrobial agent can be released in an effective amount to inhibit or prevent the outgrowth of the spoilage microorganism.

EXAMPLES

Now having described the embodiments of the present disclosure, in general, the following examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1. Synthesis pH Sensitive Core Shells for Food Spoilage Detection Using Styrene and a Glycerol-Based Biobased Dendrimeric Oligomer Containing Summary Biobased dendrimeric oligomer was successfully synthesized from glycerol, the waste from biodiesel process using abundant biomass as the feedstock. This dendrimer responds by expanding upon protonation, imparting pH sensitivity to the composite copolymer upon polymerization. Miniemulsion polymerization was used to synthesize pH sensitive core shells using styrene as a co-monomer. NMR data proved the successful incorporation of the amine dendrimer in the latex and its protonation upon pH change. Hydrophobic dye was encapsulated as a model compound which increased the particle size of the latex formed. The dye was released as a response to changing the pH of the latex solution and film. The pH sensitive polymers can be used as an indicator for the health of fresh meats and produce for food safety during storage, transport and sales. Strong visual indicators of poor food quality can immediately warn the consumers of poor quality packaged material.

Materials:

Glycerol (>99% pure); Acryloyl chloride and trimethylamine were provided by Sigma Aldrich and were used to synthesize the bio based triacrylate monomer. Solvent Blue 59 (fat soluble model dye) and Nile Red (fluorescent hydrophobic dye) was also purchased from Sigma Aldrich. Dichloromethane (99.9% pure); ethylene diamine; methanol (HPLC grade); 2, 2 Azo-isobutyronitrile (AIBN); Triton 405 (TX-405, $(C_8H_{17})$ $C_6H_4$ $(OCH_2CH_2)_{40}OH$, 70% solution in water; and hexadecane (>99%) were purchased from Fisher Scientific. Styrene (99%) was purchased from Arcos Organics. Styrene was washed with 5% (wt.) NaOH, followed by de-ionized water until pH 7 was reached, vacuum distilled at 74° C. and then used.

Synthesis of Glycerol Triacrylate Monomer

A dry three neck flask (placed in an ice bath) was connected to a Schlenk line and purged three times alternating between Nitrogen and vacuum to remove all traces of oxygen and moisture. Next, under a nitrogen atmosphere, a solution of 50 m mol glycerol, 250 m mol triethylamine and 50 ml of dichloromethane was added using syringes. Next, 250 m mol of Acryloyl chloride was carefully added dropwise within 5 min; keeping the entire solution constantly stirring. The reaction mixture was stirred at room temperature for 36 hr under Nitrogen atmosphere. Upon completion of the reaction, the mixture was filtered and the solid was further washed with dichloromethane solvent. The combined organic phase was washed with dil. HCl, $NaHCO_3$ and water successively to remove unreacted base. The washed organic phase was then dried overnight with anhydrous $MgSO_4$ and dichloromethane solvent was removed using vacuum distillation to yield pure triacrylate monomer (83% yield by wt.)

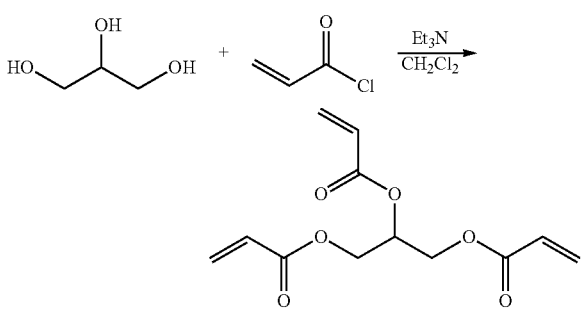

Synthesis of Glycerol Based Dendrimeric Oligomer

In a three neck flask connected with a condenser, glycerol triacrylate (synthesized) and ethylene diamine (4:1 mole ratio) was mixed with 50 ml of methanol as solvent. This reaction was stirred for 12 hr at 30° C., filtered and organic phase collected and further washed with methanol. This solution was then dried under vacuum at 30° C. for 24 hr to yield sticky, hydrophobic dendritic oligomer used for synthesis of pH sensitive polymer.

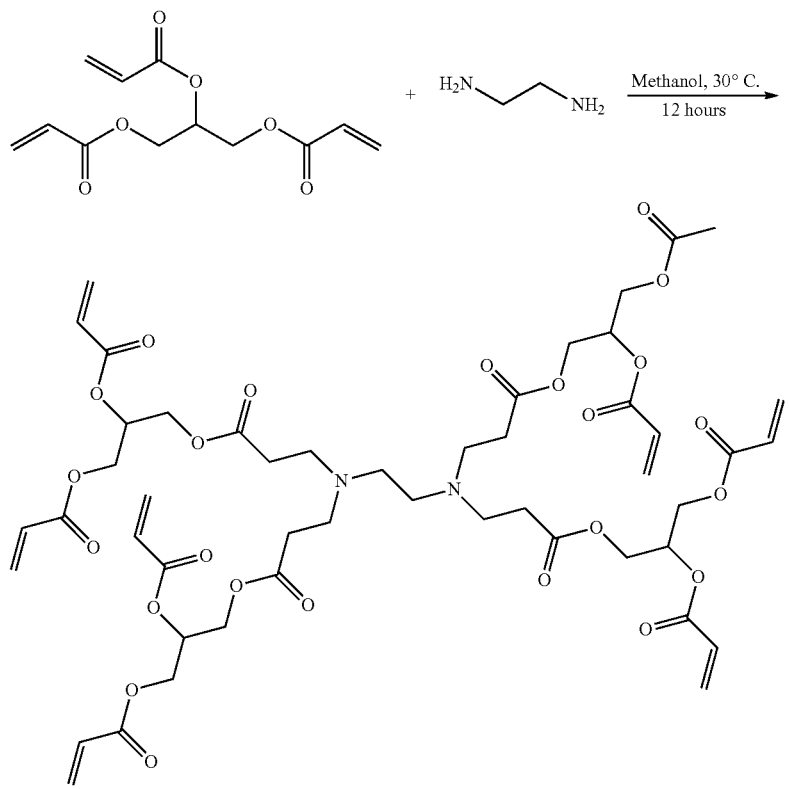

Miniemulsion Polymerization Using Styrene-Co-Dendritic Oligomer Encapsulating Hydrophobic Solvent Blue 59 Dye.

In a typical run, the oil phase contains 0.762 g of co-stabilizer hexadecane, 0.24 g AIBN, 0.024 g dye, 10 g of monomer styrene, 2 g of pH sensitive dendrimer (monomer ratio varied as 5%, 10%, 15%, 20% and 25% by wt.) were stirred at room temperature for 30 minutes followed by ultrasonication in ice bath for 4 minutes. This mixture was poured into water phase containing 1.0 g TX-405 in 100 g water and then placed in an ice bath and magnetically stirred for 30 minutes. After that, the miniemulsion was formed by ultrasonication for another 3 minutes. The resulting miniemulsion was poured into a three-neck flask equipped with a condenser and a temperature sensor and magnetically stirred for another 30 minutes at room temperature by degassing with nitrogen. The polymerization was conducted by increasing temperature to 75±2° C. and keeping at that temperature for 8 hours under continuous magnetically stirring. The reaction was terminated by adding a few drops of 2% 4-methoxy-phenol into the miniemulsion. Low percentage of dendrimer addition is due to its extremely high viscosity and the corresponding effects on the miniemulsion hence formed. The amounts of the monomer and dendrimer for the various miniemulsion polymerization reactions are shown in Table 2. 1

TABLE 2

Components for miniemulsion polymerization of styrene-co-dendritic oligomer encapsulating hydrophobic Solvent blue 59 dye with varying amount of dendrimer (wt %)

| Mixtures | Component | Amount added (g) | Percentage in total (% wt) | Percentage in monomer (wt %) |
|---|---|---|---|---|
| Oil phase A | Styrene | 11.4, 10.8, 10.2, 9.6 | 9.94, 9.43, 8.9, 8.37 | 95, 90, 85, 80 |
| | Dendrimer | 0.6, 1.2, 1.8, 2.4 | 0.52, 1.04, 1.57, | 5, 10, 15, 20 |
| | Hexadecane | 0.762 | 0.66 | 6.35 |
| | Solvent blue 59/ Nile red | 0.024 | 0.02 | 0.2 |
| | AIBN | 0.24 | 0.2 | 2 |
| Water phase B | TX-405 | 1.0 | 0.87 | 8.33 |
| | DI water | 100 | 87.31 | 833 |

Characterization

Nuclear magnetic resonance ($H^1$ NMR) proton spectra were observed in Varian Mercury 300 NMR spectrometer using $CDCl_3$ and DCI solvents. Monomer and polymer samples were dissolved in $CDCl_3$ for analysis; DCI was used to change the pH of the dendrimer and polymer synthesized to observe the spectra. TEM imaging was performed on JEOL 200CX microscope to study the morphology of polymer particles using 200 keV accelerating voltage and beam current 120 µA. A thin film of stable latex was dried on carbon type B grids and used for imaging empty core shells and dye encapsulated miniemulsion core shells. Morphology of the particles were studied at pH 7 and pH 5.4 (maintained using a phosphate buffer). Dynamic light scattering (DLS) (Zetasizer ZS3600 with a non-invasive back scatter under 500 mw, 532 nm laser, Malven, UK) was used to estimate the size and the size distribution of miniemulsion. Zeta potential of latex suspensions in pH 7 buffer and pH 5.4 buffer were estimated using Brookhaven Zetaplus instrument by phase analysis light scattering technique and using Samulchowski mobility relations at 90° incidence angle. Fluorescent spectrometry was collected using a Perkin Elmer LS 45 Fluorescent spectrometer using a 120V pulsed Xenon lamp at $\lambda_{ex}$ (371 nm) and $\lambda_{em}$ (600 nm-800 nm).

NMR Analysis of Glycerol Triacrylate, Dendrimer and Polymer

To facilitate miniemulsion polymerization, glycerol was converted to a triacrylate monomer. Acryloyl chloride was used as the acrylic acid salt during this water-sensitive esterification reaction with a triethyl amine base and dichloromethane solvent, under a steady nitrogen stream. The use of highly acidic and organic environment was to prevent the formation of water so as to push chemical equilibrium with the forward reaction. The monomer synthesized was viscous, hydrophobic and highly crosslinking. NMR analysis of the monomer in $CDCl_3$ showed high purity of monomer with the peaks that correspond to the five backbone protons of glycerol (between 4 and 4.2 ppm) and nine acrylic protons (between 5.9 and 6.2 ppm) of added side chains.

This glycerol triacrylate was used as the acidic precursor for the Michael addition reaction with a diamine. This provided the pH sensitive amine core for the dendritic structure. This dendrimer was also hydrophobic and highly viscous. After the synthesis of the dendrimeric oligomer, its NMR spectrum was also analyzed in $CDCl_3$ solvent. The results were similar to previously published reports The original peaks are seen from the acrylate system. The peak at 3.4 is the methanol peak from solvent. The amine shift is not seen due to its unprotonated neutral state.

In order to assess if the nitrogen group on the dendrimer system is incorporated in the final polymer; and if protonation is possible after polymerization, the stable latex polymer was dried, and dissolved in $CDCl_3$ to observe neutral spectrum. At neutral pH, the shift observed at 7.2 is from the chloroform solvent, the shift at 7.1 is from linear polystyrene and the shift at 3.8 is from the protons on the polymerized acrylic groups. The large peak at 1.25 is from the $CH_2$—C—$NR_2$ unprotonated amine group at neutral pH.

Next DCl was added to protonate the dissolved polymer and the organic phase was re analyzed. This deuteron is noticed in the NMR at an added peak at 1.6 as a characteristic peak for $CH_2$—C—$NR_3^+$ protonated group at low pH. This proves the presence and change in the polymer structure upon pH change and proves pH sensitivity.

Morphology of Latex Particles and Stability

Zeta potential of the latexes formed was studied to evaluate the stability of the latexes at neutral and acidic pH. As expected, the zeta potential increases significantly upon changing the pH of the latex solution and the results reported are similar to previous reports by Houillot et al., 2005[37]. The zeta potentials and (Z– average) particle sizes of each latex sample is reported in Table 3. As expected, average particle sizes decrease upon increasing the concentration of cross linker.

TABLE 3

Zeta potential and average particle size of latex particles with varying amounts of dendrimer at pH 7 and pH 5.4.

| Sample | Zeta potential (mV) | Particle size (z-average, nm) |
| --- | --- | --- |
| Empty polymer pH 7 | −21.46 | 87 |
| 5% Dendrimer pH 7 | −12.53 | 170.2 |
| 10% Dendrimer pH 7 | −12.05 | 142.6 |
| 15% Dendrimer pH 7 | −14.6 | 141.1 |
| 20% Dendrimer pH 7 | −10.8 | 121.1 |
| Empty polymer pH 5.4 | −6.06 | 110 |
| 5% Dendrimer pH 5.4 | −3.14 | 175.2 |
| 10% Dendrimer pH 5.4 | −3.02 | 142.6 |
| 15% Dendrimer pH 5.4 | −1.34 | 141.0 |
| 20% Dendrimer pH 5.4 | −2.88 | 121.6 |

Figures 2A, 2B, 2C, 2D:
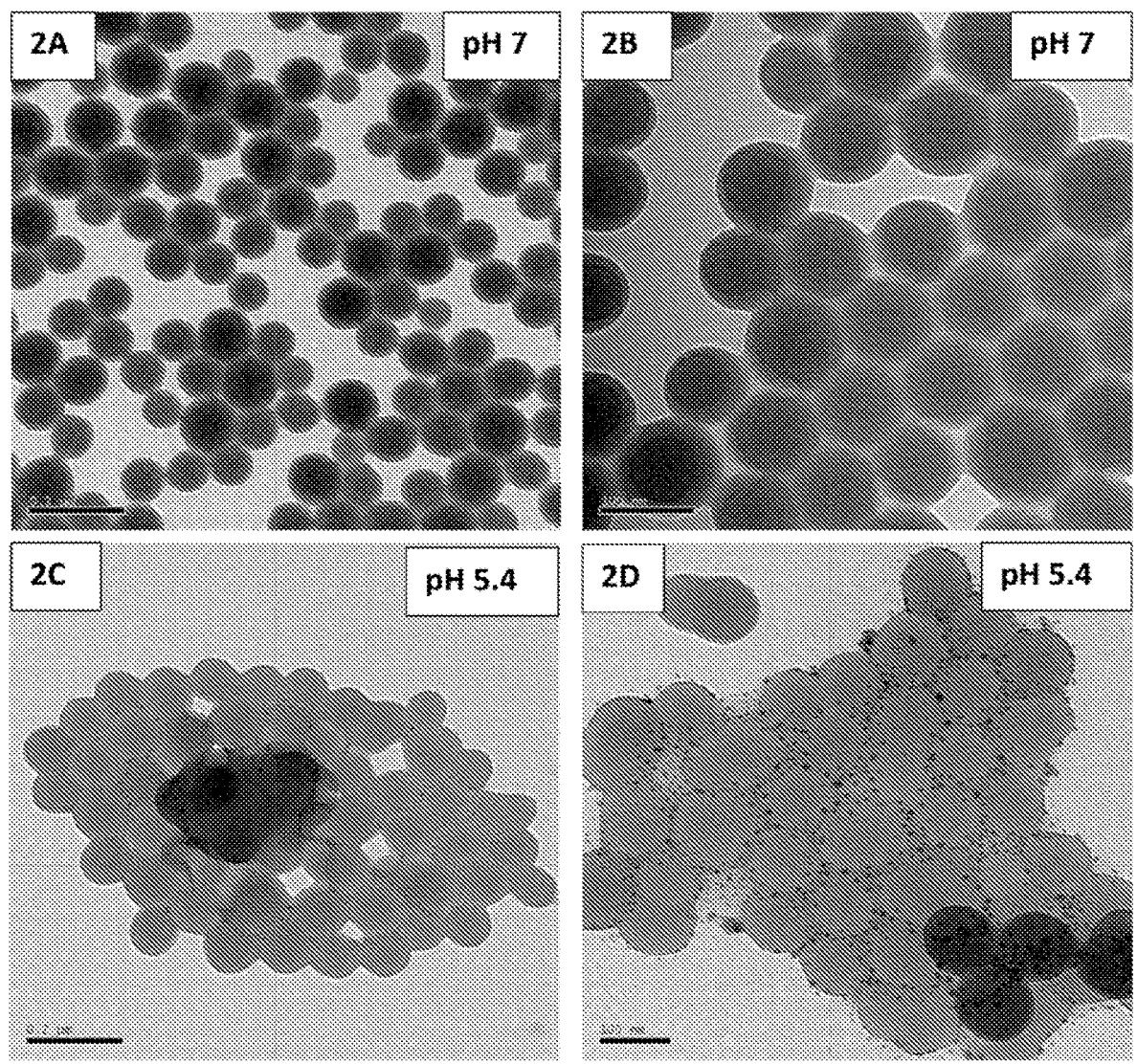
FIGS. 2A-2D are transmission electron microscope (TEM) images of pH-responsive latex particles at neutral (pH=7, FIG. 2A and FIG. 2B) and acidic (pH=5.4, FIG. 2C and FIG. 2D) conditions.

TEM imaging was performed by placing a drop of the miniemulsion on carbon B grids and drying at room temperature prior to observation. Phosphate buffer (pH 7 and pH 5.4) were used to dilute the neutral and acidic samples. The following images clearly distinguish the morphology of the particles at neutral and acidic pH. Polymer spheres are uniform in size at pH 7 as seen FIG. 2A and FIG. 2B. Upon changing the pH (FIG. 2C and FIG. 2D), the particles enlarge and the released dye is seen as spots (5-7 nm dye aggregates) on the image. The reduction in pH causes the protonation of the amine groups at each dendritic core. This protonation causes an increase in dendrimer size leading to pore formation and subsequent dye release. The rate of dye released however depended on the concentration of dendrimer and the external acidity as shown by Fluorescent spectrometry.

Fluorescent Spectrometry

Figure 3:
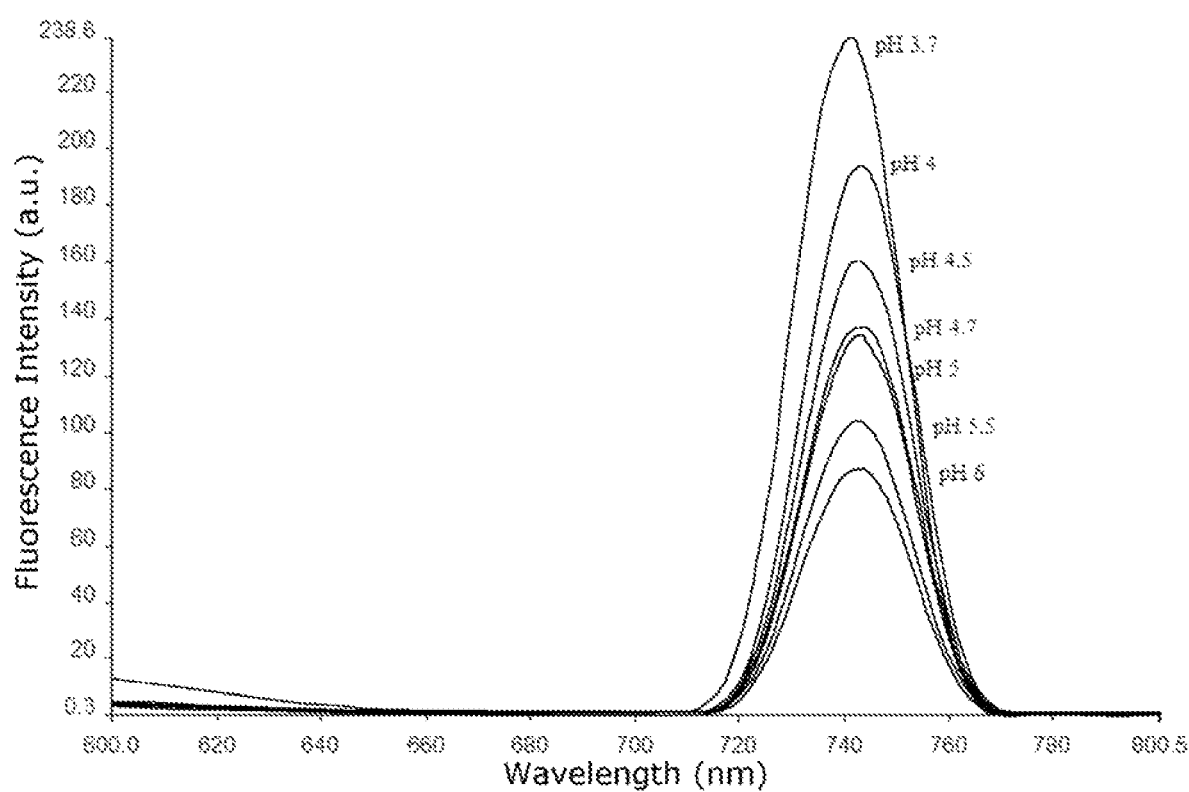
FIG. 3 is a graph of the fluorescence spectra of suspensions of latex dendrimers containing fluorescent Nile red dye as a function of pH. As the pH is decreased from 6 to 3.7 using 0.1 N HCl, the dye is released into the acetone solvent leading to an increase in the fluorescence intensity at around 743 nm.
Figure 4:
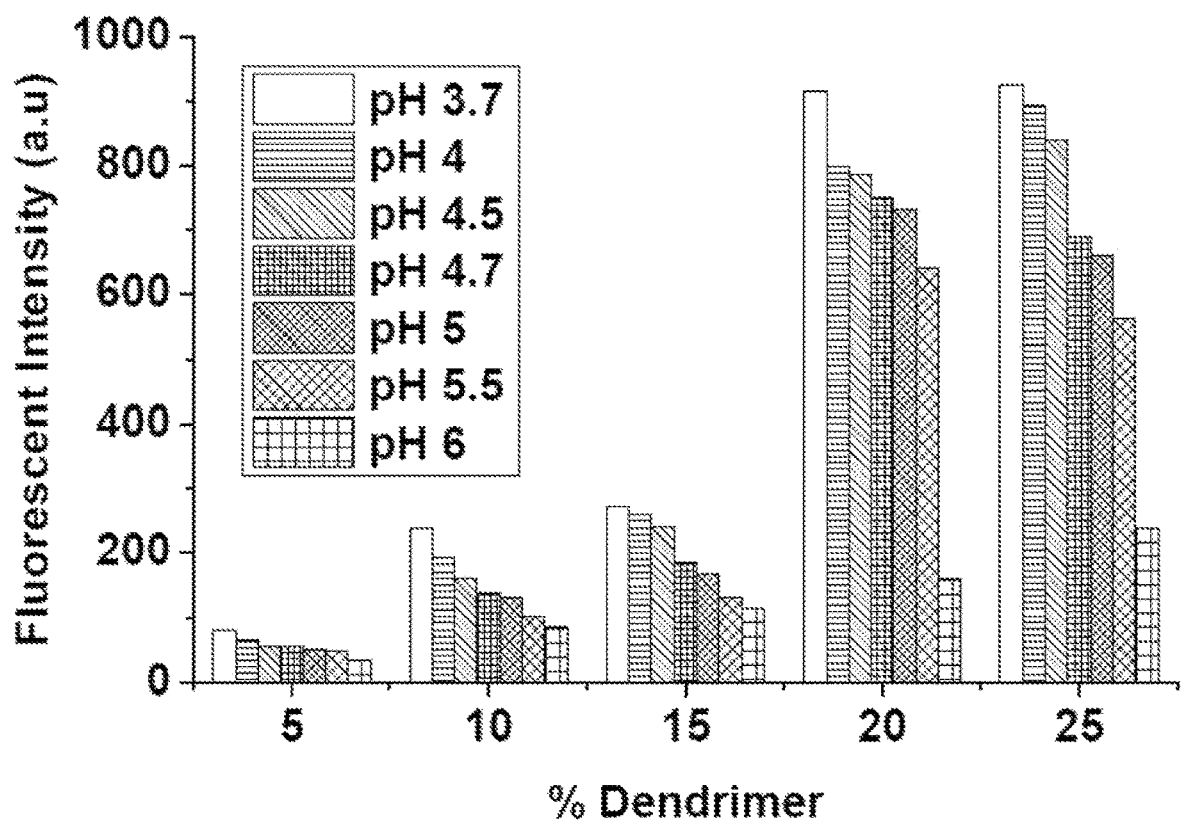
FIG. 4 is a bar graph of the fluorescence intensity (a.u.) as a function of the pH (pH=6, 6.5, 5, 4.7, 4.5, 4. And 3.7) and the percentage of dendrimer (wt %=5, 10, 15, 20, and 25 wt %) in the polymer.

The latex suspension encapsulating fluorescent Nile red dye was first dried at room temperature to form films. This dried polymer was then dissolved in acetone (0.1 g in 4 ml) and used to estimate fluorescent activity of the dye. Variation of pH was achieved using dil. HCl (0.1N) at various amounts and measured using a pH meter. As seen in FIG. 3, as the acidity of the polymer (dispersed in acetone) increased, the dye was released into the acetone phase and fluorescence increased. Maximum release of dye for each sample with varying concentration of dendrimer was seen at pH 3.7 (FIG. 4). These results are in conjunction with other similar work that deal with a one-step change in particle morphology[42]. As indicated by the results, increase fluorescence was seen by samples with high dendrimer concentrations owing to larger number of pores formed per particle and increased dye release. The films were visually inspected at varying pH (pH=7, 6.5, 5.5, 5, 4.5, 4, and 3) demonstrating the variation of the color of the films with decreasing pH. In this example, the clear progression of the red color of the Nile red dye was observed with decreasing pH.

Example 2. pH-Responsible Barrier Film of Poly (Methyl Methacrylate) Co-Glycerol-Based Dendrimeric Polymer Encapsulated Dye for Indicative Food Packaging A hydrophobic nanocomposite film was successfully synthesized for barrier food packaging with spoilage detection function. In this study, a triacrylate monomer, which could be successfully synthesized from glycerol as in Example 1, was crosslinked with ethylene diamine to produce star shaped dendrimeric structures. Next, the dendrimeric macromonomer were copolymerized with synthetic monomer (styrene or methyl methacrylate, MMA) in the presence of hydrophobic dye via minimemulsion polymerization to prepare pH-responsible core-shell structures with dye encapsulation. Gel Permeation Chromatography (GPC) along with Differential Scanning calorimetry (DSC) characterized the synthesized miniemulsion nanocomposites. The miniemulsion was further casted in vacuum to form a pH-responsible hydrophobic barrier film. Color variation of miniemulsion and its film was measured in different pH buffers and in presence of meat samples during different spoilage period. The barrier film demonstrates an excellent color variation along with the pH change at the spoilage point of pork samples. Therefore, the developed pH-responsible film has a great potential as not only a barrier film but also the diagnostic tool for food spoilage detection.

Materials

Methylene red dye (pure indicator) and Triton X-405 (70% solution in water) was purchased from Acros Organics. Ethylenediamine (99.5%) and 2-2, -Azobis (2-methylpropionitrile) (AIBN) 98% were purchased from Sigma Aldrich. Methanol (HPLC grade) and 4-Methoxy-phenol were purchased from Fischer Scientific. Methyl methacrylate (MMA) 99% was purchased from Acros Organics and utilized as acrylate monomer for polymerization. Trimethylolpropane triacrylate (TMPTA), technical grade, was used in the synthesis of dendritic oligomer and purchased from Sigma Aldrich. Pork samples were obtained from local grocery resources. Citric acid monohydrate and disodium phosphate (DSP) $Na_2HPO_4 \cdot 7H_2O$ were both utilized to make pH buffers for pH testing and purchase from Acros Organics.

Synthesis Glycerol Based Dendrimeric Macromonomers

In a three-neck flask connected to a reflux condenser, in order to further simplify the synthesis step, trimethylolpropane triacrylate (TMPTA, purified) was used to replace glycerol-based triacrylate due to their similar structures. TMPTA and ethylenediamine (5:1 mole ratio) was mixed with 50 mL of solvent, methanol. The reaction was magnetically stirred for 12 hrs at 30° C. The organic phase of the reaction product was collected, filtered, and washed with methanol. Collected solution was then dried under vacuum at 30° C. for 24 hrs to obtain the dendrimeric macromonomer for further synthesis. The reaction is expressed as below:

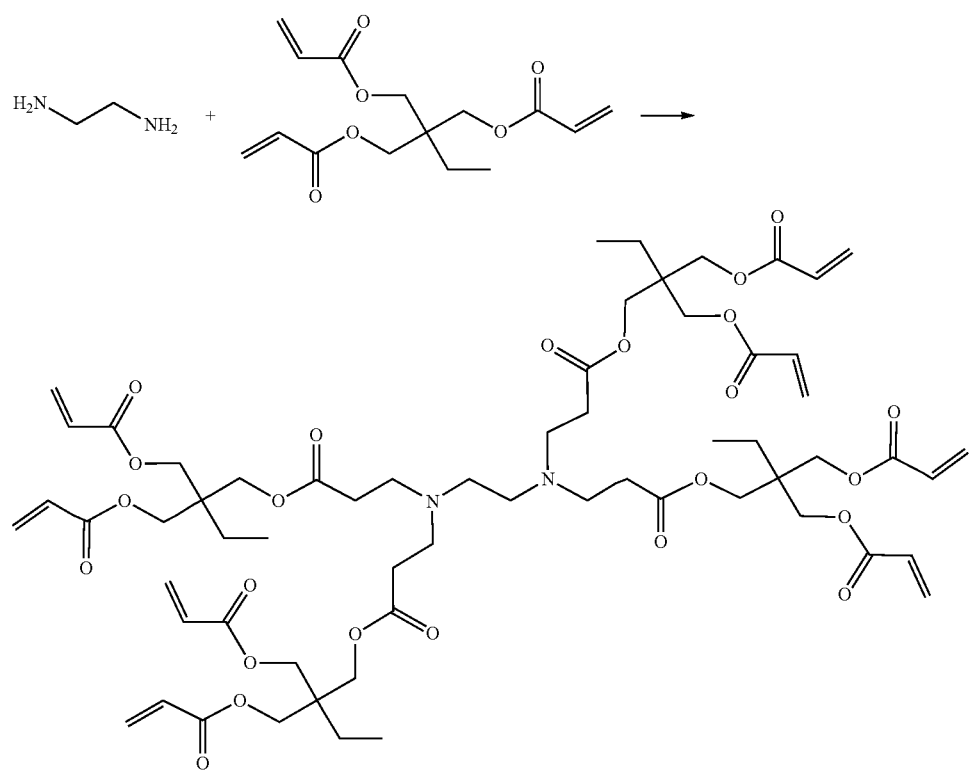

Mini-Emulsion Polymerization Using PMMA Co-Dendrimeric Oligomer Encapsulating Methylene Red Dye as Model Component Preparation of core (dendrimeric oligomer, pure indicative dye, and hexadecane)—shell (poly (methyl methacrylate) nanocomposite via miniemulsion polymerization is described as follows. In a typical run, the synthesized macromonomer (2 g) was dispersed in monomer MMA (10 g). Then they were mixed with hexadecane (0.762 g), initiator AIBN (0.24 g), and methylene red dye (0.024 g) to form oil phase. This mixture was stirred at room temperature for 30 mins and followed by ultrasonication for 4 min in ice bath. Sonicated mixture was transferred into water phase consisting of deionized water (100 g) and TX-405 (1 g). Oil-in-water phase was then placed in an ice bath and magnetically stirred for 30 mins at room temperature. After which, the miniemulsion was prepared further by ultrasonication of the mixture for 3 min in an ice bath. The resulting miniemulsion was bubbled with nitrogen and magnetically stirred for 30 min in a three-neck flask with reflux condenser and thermal sensor at room temperature. Miniemulsion polymerization was conducted at increased temperature (75±2° C.) for 8 hrs under continuous magnetically stirring. Polymerization was terminated by a few drop-by-drop additions of 2% 4-methoxy-phenol into miniemulsion. A detailed recipe of mini-emulsion polymerization is given based on varying co-monomer percentage (5%, 10%, 15%, 20%, and 20% by wt.) as shown in Table 4.

TABLE 4

Typical Miniemulsion Recipe

| Mixtures | Component | Amount added (g) | Percentage in total (wt %) | Percentage in monomer (wt %) |
|---|---|---|---|---|
| Oil phase A | MMA | 11.4, 10.8, 10.2, 9.6 | 9.94, 9.43, 8.9, 8.37 | 95, 90, 85, 80 |
| | Dendrimer | 0.6, 1.2, 1.8, 2.4 | 0.52, 1.04, 1.57, 2.09 | 5, 10, 15, 20 |
| | Hexadecane | 0.762 | 0.66 | 6.35 |
| | Methylene Red dye | 0.024 | 0.02 | 0.2 |
| | AIBN | 0.24 | 0.2 | 2 |
| Water phase B | TX-405 | 1.0 | 0.87 | 8.33 |
| | DI water | 100 | 87.31 | 833 | pH Analysis of Pork During Storage

The pork sample was stored at 4° C. (refrigerator temperature) and 25° C. (room temperature) for analysis. In a typical test, fresh pork sample(s) (2 g) was blended with 18 mL of sterile distilled water (SDW) and then vortexed for 2 min in a centrifuge tube for homogenization. All pH values were recorded by a calibrated Accumet AE150 pH meter (Fischer Scientific) by immersing the electrode in homogenized samples. Testing was conducted for 6 days and pH was measured in every 24 h. A range of pH buffers were also prepared from varying amounts of citric acid monohydrate and $Na_2HPO_4 \cdot 7H_2O$ according to the pH values measured from the pork sample during the spoilage period.

Application Test of pH-Sensitive Barrier Films on Pork

The pH-responsible nanocomposite films were prepared by first evaporation of water under vacuum less than 50° C. The film was then placed on pork samples kept in the perish dish throughout the test period (6 days). Films were tested on the pH buffers as well. The color changes of the films were identified by the photos taken during the testing period.

Characterization

Nuclear magnetic resonance ($H^1$ NMR) proton spectra were observed in Varian Mercury 300 NMR spectrometer using $CDCl_3$ and DCI solvents. Monomer and polymer samples were dissolved in $CDCl_3$ for chemical structure analysis (the data didn't show in this report since it was already shown in the prevention patent). Differential scanning calorimetry (DSC) was performed for miniemulsion films of pure PMMA, PMMA encapsulated methylene dye, and pH-sensitive PMMA-dendrimeric nanocomposite films encapsulated dye. DSC was measured on a Seiko 6200 DSC under Nitrogen at a heating rate of 10° C./min. The molecular weight of PMMA, PMMA-dye and the nanocomposite films were measured by size exclusion chromatography (SEC), an Agilent Technologies 1260 series HPLC system equipped with a refractive index detector (RID) and a multiple wavelength detector (MWD) (CA, USA). Three columns were connected in series including PLgel mixed B, PLgel mixed E 5 µm with a pore size of 10,000 Å and PLgel mixed E 5 µm with a pore size of 100 Å. Polymer films were dissolved in HPLC-grade tetrahydrofuran for 8 hours at a concentration of approximately 2.0 wt %. Then the solution was filtered through 0.22 µm syringe filter before injections to remove undissolved materials. 20 µL filtered solution was injected in each run at a thermostat temperature of 25° C. and a flow rate of 1 mL/min. All results were processed using ChemStation software package with GPC (Gas Permeation Chromatography) analysis (Rev.B. 04.03). The molecular weight was calculated based on a universal calibration using a set of polystyrene standards.

Results and Discussion

GPC Analysis of Miniemulsion Films

Figure 5:
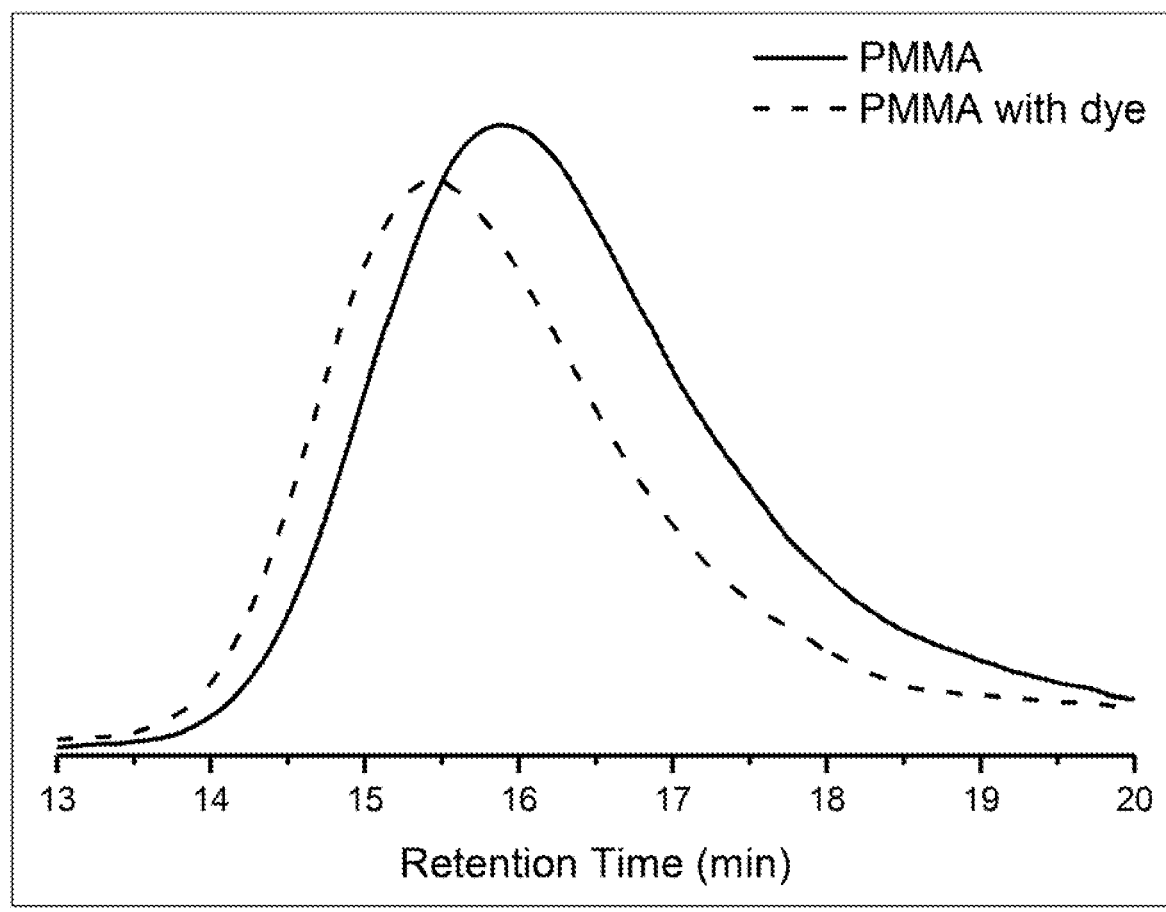
FIG. 5 is a GPC Analysis of Pure PMMA and PMMA with dye.
Figure 6:
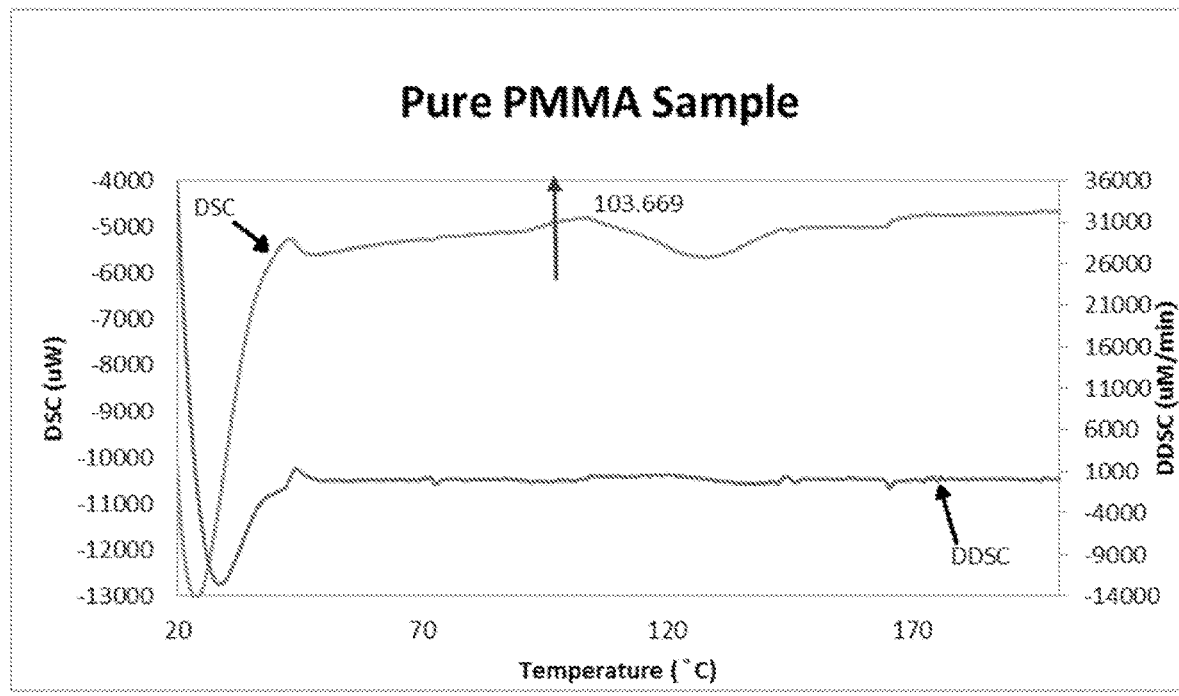
FIG. 6 is a DSC thermograph of pure PMMA sample.
Figure 7:
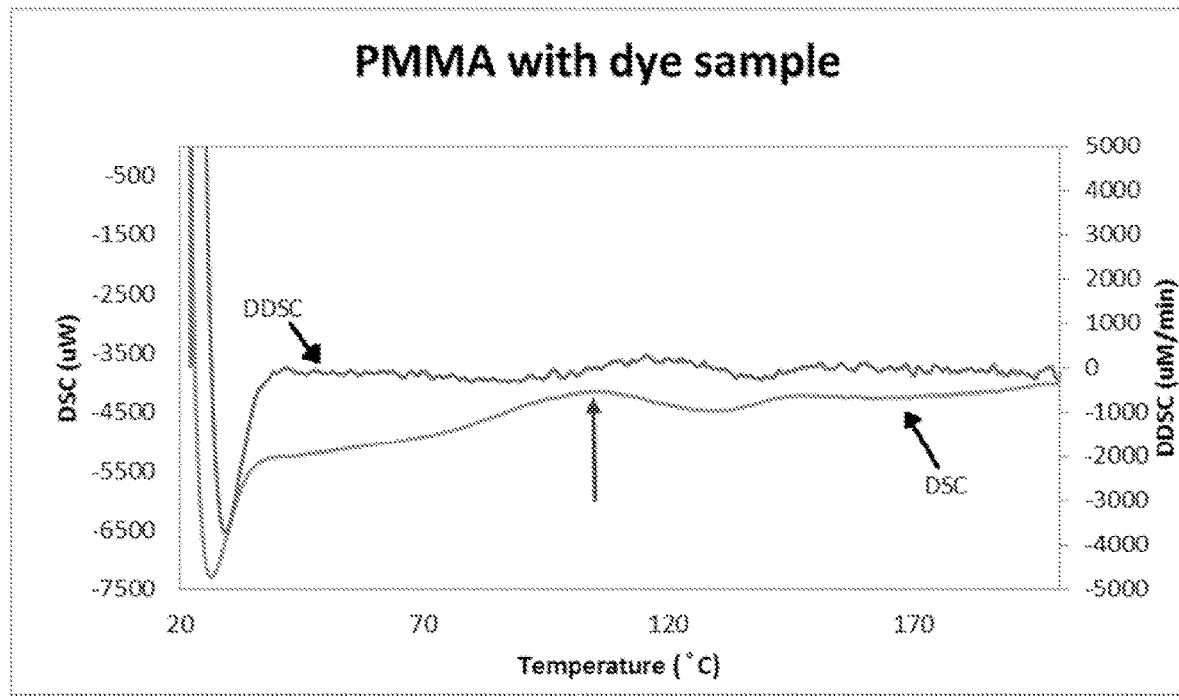
FIG. 7 is a DSC thermograph of PMMA-dye sample.

The molecular weight of the synthesized polymer and nanocomposite were measured by the SEC. Three samples were measured including Pure PMMA, PMMA with encapsulated methylene red dye, and PMMA co-dendrimeric nanocomposite with the encapsulated methylene red dye. The PMMA co-dendrimeric nanocomposite was failed to dissolve in the THF solvent and no molecular weight was detected using this method. FIG. 5 displays the multi-spectrum of pure PMMA and PMMA with dye. Table 4 also shows the molecular weight and the polydispersity of these two samples. The results indicate that PMMA with dye had much higher Mn (348.310) and Mw (885,200) than those of pure PMMA (225,590 for Mn and 583,070 for Mw). It could be explained that the hydrophobic dye might act as the costablizer or new nuclear center to promote free radical chain growth during miniemulsion polymerization. Since the glycerol-based triacrylate-based dendrimeric macromonomer was also hydrophobic, its effects on the polymerization process should be the similar as the hydrophobic dye although it could not be dissolved in the THF solvent during the measurement process.

TABLE 5

Molecular weight and its distribution of PMMA and PMMA with dye

| | PMMA | PMMA with Dye |
|---|---|---|
| Mn | 225,590 | 348,310 |
| Mw | 583,070 | 885,200 |
| polydispersity index | 2.58 | 2.54 |

DSC Analysis of Miniemulsion Films

Thermal properties of polymer or nanocomposite films were investigated by DSC analysis. To obtain glass transition of polymer or composite, temperature was increased ranging from 20 to 250° C. at a heating rate of 10° C./min under nitrogen flowing atmosphere (100 mL/min). Samples were prepared in aluminum pan and ran for two cycles with a constant maximum temperature hold for 5 min. Three samples were conducted including pure PMMA, PMMA encapsulated with methylene red dye, and PMMA co-dendrimeric polymer encapsulated with dye.

Analysis of pH-Responsive Miniemulsions and Films by Color Indication

The pH-responsible films and corresponding miniemulsions were investigated for their pH-responsive color indicating properties. Evaluation of films and emulsions were observed in varying pH buffer solutions (pH 2.6-10.0). Dried films with excellent water resistance and successful non-leaching of hydrophobic dye were visually measured as well. Miniemulsions with glycerol-based dendrimers and indicative dye in demonstrated visible color changes, ranging from pink to yellow when placed in pH buffers of increasing pH (observations were made in buffers at pH of 2.6, 3.0, 4.0, 5.0, 6.0, 7.0, 8.0, 9.2, 9.4, and 10.0). The miniemulsion in pH buffers appeared pink in pH 2.67, pinkish-yellow in 6.0, and yellowish-orange in 10.0. As pH increased further, apparent color change enhanced.

Similarly, the color variance of pH-responsive nanocomposite films with encapsulated dye varied from red to orange in buffers ranging from 3.0 to 7 (observations were made of films in buffers of pH 3.0, 4.0, 4.5, 5.0, 5.5, 6.5, and 7.0). A deep red was observed from lower pH values (3.0-4.0) and an intense orange color was seen in higher pH values (6.5-7.0). When pH was higher than 6, the buffer solution penetrated into the film and changed the transparent film to yellow. Below pH 6, the nanoparticles were enlarged and pores were possibly formed due to the protonation of tertiary amine. The pore might allow the penetration of buffer solution and the dye release to the surface, which resulted in the change of the film color from orange to dark red. This result verifies that the glycerol-based nanocomposite film could form a pH-sensitive barrier film within a 0.5 pH interval. The results of color variations within miniemulsions and films at different pH suggest stable polymerization and encapsulation of pure indicator dye could develop a rough color indicator film for food packaging material. The precise color changes (less than 0.5 pH interval) of miniemulsion solutions and films with encapsulated methylene red dye and dendritic oligomer are attributed to the pH-responsible property of the dendrimeric components in the nanocomposite film. It is worthy to mention that the color difference between miniemulsions and films is because of different loading of dye in the miniemulsion recipe and different comonomer (styrene) in the synthesis recipe.

Figure 8:
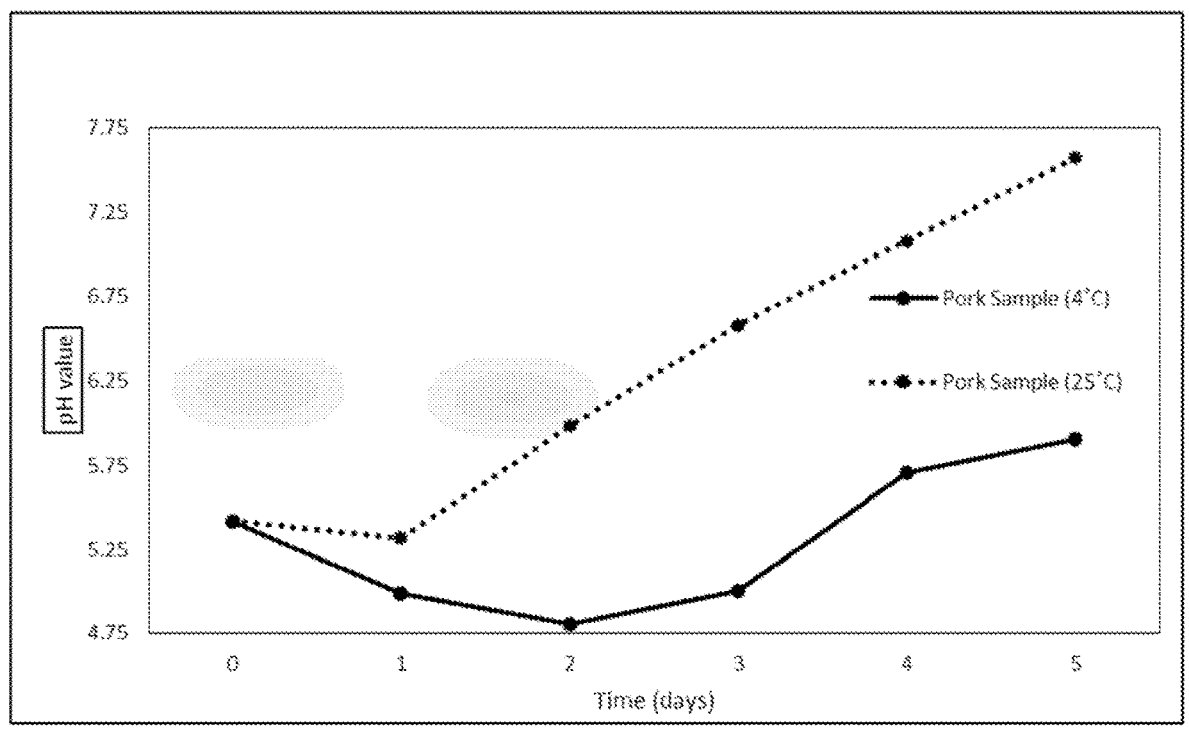
FIG. 8 is a graph of the pH changes of pork samples visible by color variation of pH-responsible films on pork samples under 25° C. and 4° C. storage temperature for different time periods.

Relationship Between pH Variation of Pork and Color Variation of Encapsulated Dye Indicator A pH analysis of pork samples and an application test of pH-responsive films were conducted to demonstrate the relationship regarding pH changes in pork with and without pH-responsive films. Analyzed pork samples placed in controlled storage conditions at room temperature (25° C.) and (4° C.) for comparative testing purposes. Initially, as seen in FIG. 8, a fresh pork sample was observed at pH 5.42. The pH value of pork was increased with the pork storage time. The pH value increased to 5.90 and 7.57 after 5 days of storage for samples at 4° C. and 25° C., individually. Meanwhile pH-responsible nanocomposite films showed a readily ascertainable color change from pH 5.42 and 7.57. Observation of increased pork pH values at both stored temperatures could be attributed to the formation of spoilage substances (e.g. ammonia) due to the decomposition of compounds such as protein and lipid (Choi et al., 2016).

The application test of pH-responsive films was performed at increased storage time at both stored temperatures 25° C. and 4° C. At both temperature, after 24 hours, pure PMMA film depicted no any color change and kept a clear and/or transparent film. This is because the pure PMMA film didn't possess any pH indicator function. The color change was observed for the PMMA encapsulated dye film at day 1, 3 and 5, individually. The results demonstrated that a color change from deep red, middle red to bright orange at day 1, 3 and 5, individually. Simultaneously, the pH-responsible nanocomposite film showed color change from deep red, deep orange, and bright orange at day 1, 3, and 5. The difference between these two samples is because the PMMA-encapsulated-dye film had no controllable dye release function but the pH-responsible dye release film has controllable dye release function. Thus, the developed pH-responsible films can be implemented as a real-time, visual indicative method to detect food spoilage and quality of meat products. Meanwhile, this hydrophobic nanocomposite film in combination with other synthetic polymer or hydrophobic biopolymer could be a good candidate as the packaging film to prevent water penetration as well.

CONCLUSION

In this example, a poly (methyl methacrylate, MMA) co-glycerol-based dendrimeric copolymer encapsulated dye miniemulsion film was synthesized for a water-resistant barrier film pending a pH sensor. The color variation of the barrier film could be tuned according to the loading of dendrimeric oligomers for controllable release of the encapsulated dye. The GPC data proved the successful synthesis of copolymer. DSC proved the thermoplastic properties of the copolymer and the proper glass transition temperature. The hydrophobic, pH-responsible bionanocomposite film was obtained by casting of miniemusion latex under vacuum without dye leaching. The color change of the hydrophobic film on pork samples provides a precisely, real-time, simple, and visual method to detect the quality change of food products in most food spoilage range (4-7) within a narrow pH (0.5) interval. The inclusion of glycerol-based dendrimeric macromonomer not only provides the precise pH indication function but also reduces the package waste with the presence of thin nanoshell structure. This nanocomposite barrier film with a pH sensor has a great potential as both a hydrophobic barrier packaging film and a diagnostic tool to assure food safety and quality. Further works of this study need to focus on improvement of the synthesis of dendrimeric oligomer. Physical properties need to be further explored for the improvement of polymer films.

REFERENCES FOR EXAMPLE 2

Arvanitoyannis, I., Biliaderis, C. G., Ogawa, H., Kawasaki, N. 1998. Biodegradable films made from low-density polyethylene (LDPE), rice starch and potato starch for food packaging applications: Part 1. Carbohydrate Polymers, 36(2), 89-104.

Barnes, E. M., Impey, C. 1968. Psychrophilic spoilage bacteria of poultry. Journal of Applied Bacteriology, 31(1), 97-107.

Borch, E., Kant-Muermans, M.-L., Blixt, Y. 1996a. Bacterial spoilage of meat and cured meat products. International journal of food microbiology, 33(1), 103-120.

Chen, X., & Gu, Z. (2013). Absorption-type optical pH sensitive film based on immobilized purple cabbage pigment. Sensors and Actuators B: Chemical, 178, 207-211.

Choi, I., Lee, J. Y., Lacroix, M., & Han, J. (2017). Intelligent pH indicator film composed of agar/potato starch and anthocyanin extracts from purple sweet potato. Food chemistry, 218, 122-128.

Dalgaard, P. 1995. Qualitative and quantitative characterization of spoilage bacteria from packed fish. International Journal of Food Microbiology, 26(3), 319-333.

Dainty, R. 1996. Chemical/biochemical detection of spoilage. International journal of food microbiology, 33(1), 19-33.

Ellis, D. I., Goodacre, R. 2001. Rapid and quantitative detection of the microbial spoilage of muscle foods: current status and future trends. Trends in Food Science & Technology, 12(11), 414-424.

Gram, L., Dalgaard, P. 2002. Fish spoilage bacteria—problems and solutions. Current opinion in biotechnology, 13(3), 262-266.

Gram, L., Huss, H. H. 1996. Microbiological spoilage of fish and fish products. International journal of food microbiology, 33(1), 121-137.

Korkeala, H., Alanko, T., Mäkelä, P., Lindroth, S. 1990. Lactic acid and pH as indicators of spoilage for vacuum-packed cooked ring sausages. International journal of food microbiology, 10(3), 245-253.

Lee, J.-W., Son, S.-M., Hong, S.-I. 2008. Characterization of protein-coated polypropylene films as a novel composite structure for active food packaging application. Journal of Food Engineering, 86(4), 484-493.

Pacquit, A., Frisby, J., Diamond, D., Lau, K. T., Farrell, A., Quilty, B., Diamond, D. 2007. Development of a smart packaging for the monitoring of fish spoilage. Food Chemistry, 102(2), 466-470.

Pacquit, A., Lau, K. T., McLaughlin, H., Frisby, J., Quilty, B., Diamond, D. 2006. Development of a volatile amine sensor for the monitoring of fish spoilage. Talanta, 69(2), 515-520.

Park, H. J., Chinnan, M. S. 1995. Gas and water vapor barrier properties of edible films from protein and cellulosic materials. Journal of Food Engineering, 25(4), 497-507.

Pereira, V. A., de Arruda, I. N. Q., & Stefani, R. (2015). Active chitosan/PVA films with
anthocyanins from *Brassica oleraceae* (Red Cabbage) as time—temperature indicators for
application in intelligent food packaging. *Food Hydrocolloids*, 43, 180-188.

Pexara, E. S., Metaxopoulos, J., Drosinos, E. H. 2002. Evaluation of shelf life of cured, cooked, sliced turkey fillets and cooked pork sausages—rpiroskr—stored under vacuum and modified atmospheres at +4 and +10° C. Meat science, 62(1), 33-43.

Samelis, J., Kakouri, A., Georgiadou, K., Metaxopoulos, J. 1998. Evaluation of the extent and type of bacterial contamination at different stages of processing of cooked ham. Journal of applied microbiology, 84(4), 649-660.

Samelis, J., Kakouri, A., Rementzis, J. 2000. The spoilage microflora of cured, cooked turkey breasts prepared commercially with or without smoking. International journal of food microbiology, 56(2), 133-143.

Schirmer, B., Heir, E., Langsrud, S. 2009. Characterization of the bacterial spoilage flora in marinated pork products. Journal of applied microbiology, 106(6), 2106-2116.

Scheu, P. M., Berghof, K., Stahl, U. 1998. Detection of pathogenic and spoilage micro-organisms in food with the polymerase chain reaction. Food microbiology, 15(1), 13-31.

Smolander, M., Ahvenainen, R. 2003. The use of freshness indicators in packaging. Novel food packaging techniques, 127-143.

Vihavainen, E. J., Björkroth, K. J. 2007. Spoilage of value-added, high-oxygen modified-atmosphere packaged raw beef steaks by *Leuconostoc gasicomitatum* and *Leuconostoc gelidum*. International journal of food microbiology, 119(3), 340-345.

Veiga-Santos, P., Ditchfield, C., Tadini, C. 2011. Development and evaluation of a novel pH indicator biodegradable film based on cassava starch. Journal of Applied Polymer Science, 120(2), 1069-1079.

Weber, C., Haugaard, V., Festersen, R., Bertelsen, G. 2002. Production and applications of biobased packaging materials for the food industry. Food Additives & Contaminants, 19(S1), 172-177.

Weber, C. J. 2000. Biobased packaging materials for the food industry: Status and perspectives, a European concerted action.

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A nanoparticle for the detection of food spoilage, the nanoparticle comprising:
a hydrophobic core comprising a hydrophobic dye; and
a copolymer of a hydrophobic polymer repeat unit and a pH responsive dendrimer repeat unit,
wherein the pH responsive dendrimer repeat unit has a structure according to the following formula or a derivative thereof,

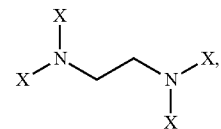

wherein each occurrence of X is independently a branched acrylate arm having a structure according to the following formula

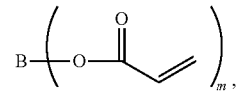

wherein each occurrence of B is a substituted or unsubstituted, linear or branched alkyl, heteroalkyl, alkenyl, alkynyl, carbocyclic, or heterocyclic group,
wherein m is an integer of 2 to 8,
wherein the pH responsive dendrimer repeat unit is present at an amount from about 5 wt % to 20 wt % based upon the weight of the copolymer,
wherein the nanoparticle is chemically stable and has a diameter of about 50 nm to 200 nm at neutral pH, and
wherein the nanoparticle releases the hydrophobic dye at a pH range of about 4.5 to 6.7 to indicate the food spoilage.

2. The nanoparticle according to claim 1, wherein the pH responsive dendrimer repeat unit has a structure according to the following formula

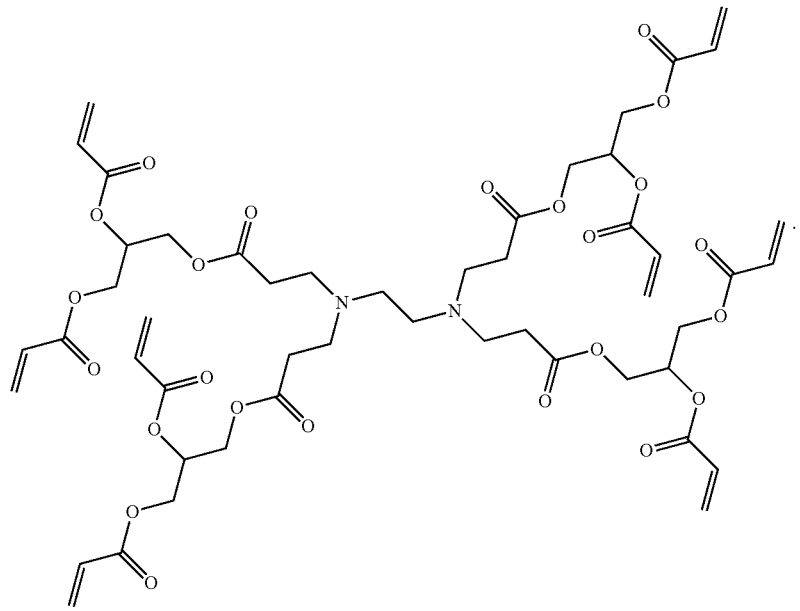

3. The nanoparticle according to claim 1, wherein the pH responsive dendrimer repeat unit has a structure according to the following formula

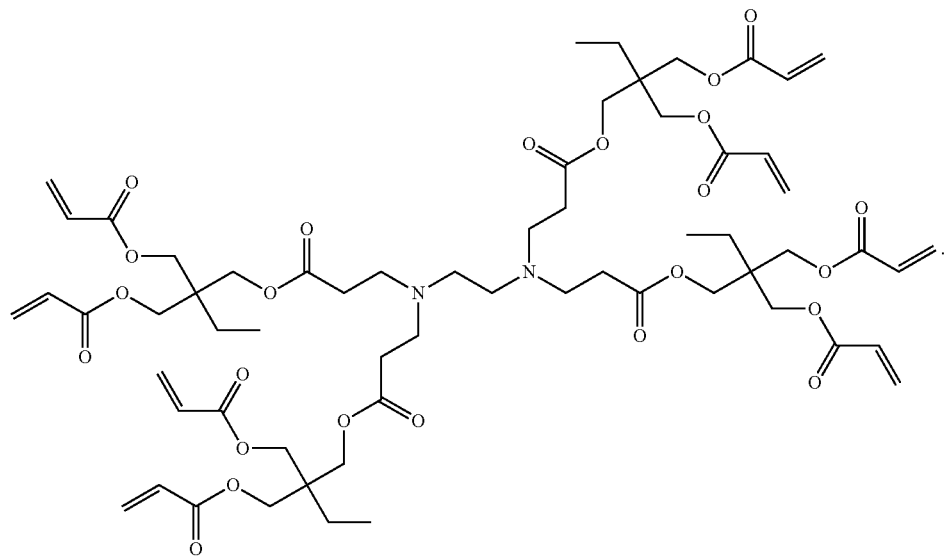

4. The nanoparticle of claim 1, wherein the nanoparticle has a diameter of 50 nm to 250 nm.

5. The nanoparticle of claim 1, wherein the hydrophobic polymer repeat unit is selected from the group consisting of a fluorocarbon, a tetrafluoroethylene, a vinylfluoride, a siloxane, a dimethylsiloxane, butadiene, a methacrylate, ethylene, an olefin, styrene, propylene, and an oligomer thereof.

6. A packaged food product comprising:
a food product;
   a packaging containing the food product; and
   a composition comprising a plurality of the nanoparticles according to claim 1.

7. The packaged food product according to claim 6, wherein the pH responsive dendrimer repeat unit has a structure according to the following formula

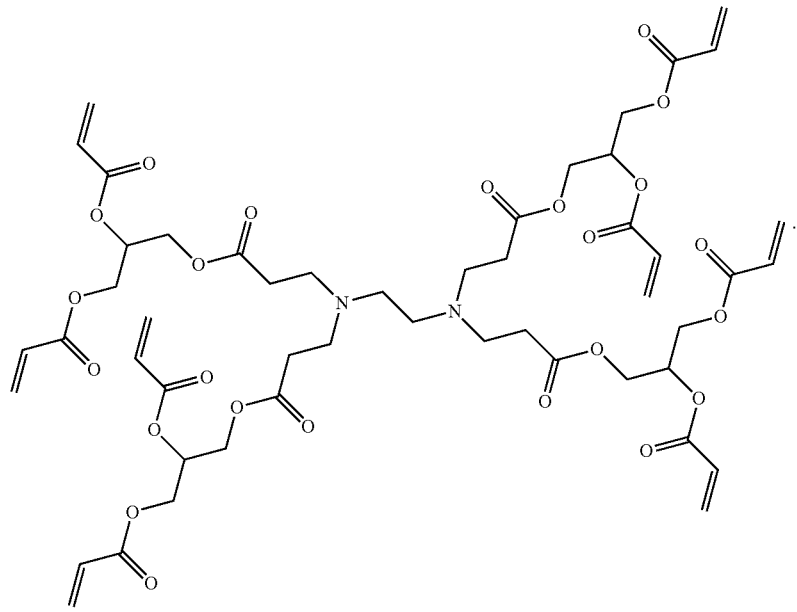

8. The packaged food product according to claim 6, wherein the pH responsive dendrimer repeat unit has a structure according to the following formula

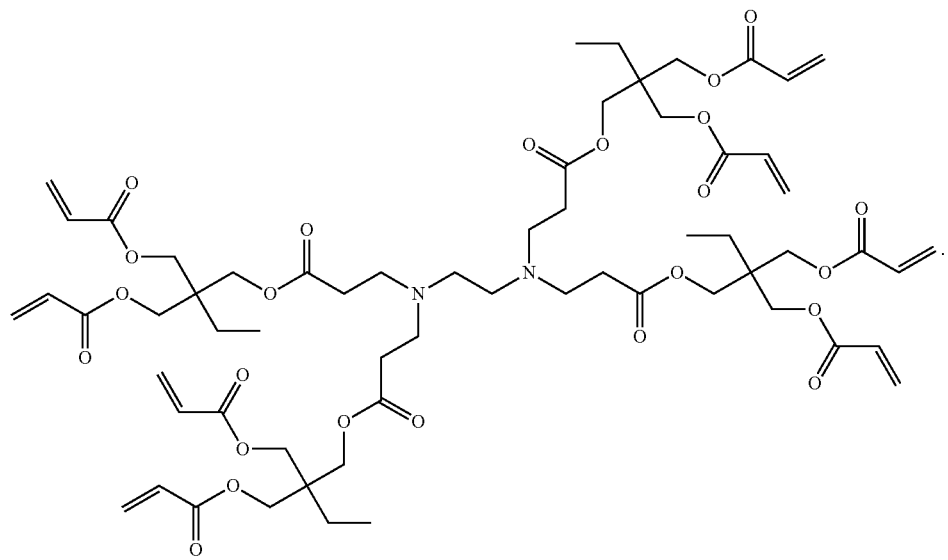

9. The packaged food product of claim 6, wherein the food product is selected from the group consisting of beef, pork, poultry, and fish.

10. The packaged food product of claim 6, wherein the packaged food product is a ready-to-eat food product.

11. The packaged food product of claim 6, wherein the composition is part of the packaging and is in contact with the food product inside the packaging; and wherein a release of the hydrophobic active agent indicates the food has spoiled, inhibits or prevents the growth of a food spoilage microorganism, or both.

* * * * *